(12) United States Patent
Burns

(10) Patent No.: US 12,133,763 B2
(45) Date of Patent: Nov. 5, 2024

(54) ULTRASOUND IMAGING

(71) Applicant: BRUIN BIOMETRICS, LLC, Los Angeles, CA (US)

(72) Inventor: Martin F. Burns, Los Angeles, CA (US)

(73) Assignee: BRUIN BIOMETRICS, LLC, Los Angeles, CA (US)

( * ) Notice: Subject to any disclaimer, the term of this patent is extended or adjusted under 35 U.S.C. 154(b) by 194 days.

(21) Appl. No.: 17/776,759

(22) PCT Filed: Nov. 11, 2020

(86) PCT No.: PCT/US2020/060062
§ 371 (c)(1),
(2) Date: May 13, 2022

(87) PCT Pub. No.: WO2021/096992
PCT Pub. Date: May 20, 2021

(65) Prior Publication Data
US 2022/0401063 A1    Dec. 22, 2022

Related U.S. Application Data

(60) Provisional application No. 63/108,627, filed on Nov. 2, 2020, provisional application No. 62/935,635, filed on Nov. 14, 2019.

(51) Int. Cl.
*A61B 8/00* (2006.01)
*A61B 8/08* (2006.01)

(52) U.S. Cl.
CPC ............ *A61B 8/085* (2013.01); *A61B 8/0858* (2013.01); *A61B 8/461* (2013.01); *A61B 8/5207* (2013.01); *A61B 8/5223* (2013.01)

(58) Field of Classification Search
CPC ....... A61B 8/085; A61B 8/0858; A61B 8/461; A61B 8/5207; A61B 8/5223
See application file for complete search history.

(56) References Cited

U.S. PATENT DOCUMENTS

| | | | |
|---|---|---|---|
| 5,010,772 A | 4/1991 | Bourland et al. | |
| 6,287,253 B1 | 9/2001 | Ortega et al. | |

(Continued)

FOREIGN PATENT DOCUMENTS

| | | | |
|---|---|---|---|
| CA | 2620288 A1 | 8/2009 | |
| JP | 2004-105446 A | 4/2004 | |

(Continued)

OTHER PUBLICATIONS

Supplementary European Search Report for European Application 20886304, completed May 30, 2023.

(Continued)

*Primary Examiner* — Joel F Brutus
(74) *Attorney, Agent, or Firm* — Arnold & Porter Kaye Scholer LLP

(57) ABSTRACT

The present disclosure provides methods and apparatus for evaluating tissue structure in damaged or healing tissue. The present disclosure also provides methods of identifying a patient at the onset of risk of pressure ulcer or at risk of the onset of pressure ulcer, and treating the patient with anatomy-specific clinical intervention selected based on a number of sonographic characteristics. The present disclosure also provides methods of stratifying groups of patients based on risk of wound development and methods of reducing incidence of tissue damage in a care facility. The present disclosure also provides methods to analyze trends of sonographic characteristics to detect tissue damage before it is visible, and methods to compare bisymmetric sonographic characteristics to identify damaged tissue.

20 Claims, 9 Drawing Sheets

(56) References Cited

U.S. PATENT DOCUMENTS

| | | | |
|---|---|---|---|
| 9,320,665 | B2 | 4/2016 | Main et al. |
| 10,020,075 | B2 | 7/2018 | Perlman et al. |
| 2003/0220581 | A1 | 11/2003 | Ollmar et al. |
| 2007/0197904 | A1 | 8/2007 | Viglianti et al. |
| 2008/0132808 | A1 | 6/2008 | Lokhorst et al. |
| 2008/0194928 | A1 | 8/2008 | Bandic et al. |
| 2008/0279438 | A1 | 11/2008 | West et al. |
| 2009/0068685 | A1 | 3/2009 | Streeper et al. |
| 2010/0172567 | A1 | 7/2010 | Prokoski |
| 2011/0215930 | A1 | 9/2011 | Lee et al. |
| 2011/0301441 | A1 | 12/2011 | Bandic et al. |
| 2012/0232403 | A1 | 9/2012 | Smith |
| 2013/0006151 | A1 | 1/2013 | Main et al. |
| 2014/0092288 | A1 | 4/2014 | Hattery et al. |
| 2016/0113667 | A1 | 4/2016 | Bailey et al. |
| 2016/0135731 | A1 | 5/2016 | Drennan |
| 2016/0253800 | A1* | 9/2016 | Gurevich ............... G16H 50/50 382/128 |
| 2017/0196489 | A1 | 7/2017 | Horras et al. |
| 2017/0224271 | A1 | 8/2017 | Lachenbruch et al. |
| 2017/0311807 | A1 | 11/2017 | Fu et al. |
| 2017/0325683 | A1 | 11/2017 | Larson et al. |
| 2017/0347891 | A1 | 12/2017 | Rogers et al. |
| 2018/0042483 | A1 | 2/2018 | Bardhan et al. |
| 2018/0098727 | A1 | 4/2018 | Spahn et al. |
| 2019/0021650 | A1 | 1/2019 | Lee et al. |
| 2019/0100802 | A1 | 4/2019 | Sanada et al. |
| 2019/0104982 | A1 | 4/2019 | Dunn et al. |
| 2019/0125248 | A1 | 5/2019 | Curtin |
| 2019/0142333 | A1 | 5/2019 | Burns et al. |
| 2019/0160116 | A1 | 5/2019 | Muller et al. |
| 2019/0175098 | A1 | 6/2019 | Burns et al. |
| 2019/0246972 | A1 | 8/2019 | Burns et al. |
| 2019/0307904 | A1* | 10/2019 | Ballamy ................. A61L 15/60 |
| 2022/0386941 | A1 | 12/2022 | Burns |
| 2022/0395235 | A1 | 12/2022 | Burns |
| 2022/0400956 | A1 | 12/2022 | Burns |
| 2022/0401015 | A1 | 12/2022 | Burns |

FOREIGN PATENT DOCUMENTS

| | | |
|---|---|---|
| JP | 2016-224396 A | 12/2016 |
| JP | 2017-012427 A | 1/2017 |
| JP | 2018-089368 A | 6/2018 |
| JP | 2018-093901 A | 6/2018 |
| WO | 2019/099810 A1 | 5/2019 |
| WO | 2019/178583 A1 | 9/2019 |
| WO | 2021/096993 A1 | 5/2021 |
| WO | 2021/096994 A9 | 5/2021 |
| WO | 2021/096996 A1 | 5/2021 |
| WO | 2021/097033 A1 | 5/2021 |
| WO | 2021/097037 A2 | 5/2021 |
| WO | 2021/097079 A1 | 5/2021 |
| WO | 2021/097081 A1 | 5/2021 |
| WO | 2021/097083 A1 | 5/2021 |

OTHER PUBLICATIONS

Supplementary European Search Report for European Application 20888629, completed May 30, 2023.
Aoi et al., "Ultrasound Assessment of Deep Tissue Injury in Pressure Ulcers: Possible Prediction of Pressure Ulcer Progression," *Plastic and Reconstructive Surgery*, 124(2):542-549 (2009).
Bergstrom et al., "The Braden Scale for Predicting Pressure Sore Risk," *Nurs. Res.*, 36(4):205-210 (1987), Lippincott Williams & Wilkins (publisher), Philadelphia, PA.
Brem et al., "High Cost of Stage IV Pressure Ulcers," *Am. J. Surg.*, 200(4):473-477 (2010), Elsevier (publisher), Amsterdam, Netherlands.
Garcia-Fernandez, "Predictive Capacity of Risk Assessment Scales and Clinical Judgment for Pressure Ulcers: A Meta-Analysis," *Journal of Wound Ostomy & Commence Nursing*, 41:24-34 (2014), Lippincott Williams & Wilkins (publisher), Philadelphia, PA.
Huong et al., "Multispectral Imaging of Acute Wound Tissue Oxygenation," *J. Innov. Opt. Health Sci.*, 10(3):1750004, 8 pp. (2017), World Scientific Publishing Co. Pte Ltd. (publisher), Singapore.
International Search Report for PCT/US2020/060067 dated Mar. 17, 2021.
International Search Report for PCT/US2020/060211 dated Mar. 17, 2021.
International Search Report for PCT/US2020/060062 dated Mar. 18, 2021.
International Search Report for PCT/US2020/060063 dated Mar. 18, 2021.
International Search Report for PCT/US2020/060219 dated Mar. 18, 2021.
International Search Report for PCT/US2020/060064 dated Mar. 25, 2021.
International Search Report for PCT/US2020/060145 dated Mar. 25, 2021.
International Search Report for PCT/US2020/060222 dated Mar. 25, 2021.
International Search Report for PCT/US2020/060151 dated May 7, 2021.
The National Institute for Health and Care Excellence (NICE), "Pressure Ulcers: Prevention and Management," Clinical Guideline, 29 pp. (Apr. 23, 2014), National Institute for Health and Care Excellence (publisher), London, England.
Nelissen et al., "An Advanced Magnetic Resonance Imaging Perspective on the Etiology of Deep Tissue Injury," *J. Appl. Physiol.*, 124(6):1580-1596 (2018), American Physiological Society (publisher), Rockville, Maryland.
Pancorbo-Hidalgo et al., "Risk Assessment Scales for Pressure Ulcer Prevention: A Systematic Review," *Journal of Advanced Nursing*, 54:94-110 (2006), Wiley (publisher), Hoboken, New Jersey.
Ruan et al., "Magnetic Resonance Imaging of Nonhealing Pressure Ulcers and Myocutaneous Flaps," *Archives of Physical Medicine and Rehabilitation*, 79(9):1080-1088 (1998), Elsevier (publisher), Amsterdam, Netherlands.
Yafi et al., "Quantitative Skin Assessment Using Spatial Frequency Domain Imaging (SFDI) in Patients with or at High Risk for Pressure Ulcers," *Lasers in Surgery and Medicine*, 49(9):827-834 (2017), Wiley-Liss Inc. (publisher), New York, NY.
Yudovsky et al., "Assessing Diabetic Foot Ulcer Development Risk with Hyperspectral Tissue Oximetry," *J. Biomed. Optics*, 16(2):026009, 8 pp. (2011), SPIE (publisher), Bellingham, WA.
Kanno et al., "Low-Echoic Lesions Underneath the Skin in Subjects with Spinal-Cord Injury," *Spinal Cord*, 47:225-229 (2009).
Scheiner et al., "Ultrasound to Detect Pressure-Related Deep Tissue Injuries in Adults Admitted Via the Emergency Department: A Prospective, Descriptive, Pilot Study," *Ostomy Wound Management*, 63(3):36-46 (2017).
Supplementary European Search Report for European Application 20887519, completed Oct. 11, 2023.
Yabunaka et al., "Three-Dimensional Ultrasound Imaging of the Pressure Ulcer. A Case Report," *Med. Ultrason.*, 17(3):404-406 (2015).

* cited by examiner

ULTRASOUND IMAGING

CROSS-REFERENCE TO RELATED APPLICATIONS

This application is a U.S. National Stage under 35 U.S.C. § 371 of International Application No. PCT/US2020/060062 filed Nov. 11, 2020 (published as WO 2021/096992 on May 20, 2021), which claims the benefit of priority of U.S. Provisional Application 62/935,635 filed Nov. 14, 2019, and U.S. Provisional Application 63/108,627 filed Nov. 2, 2020, each of which is herein incorporated by reference in its entirety.

FIELD

The present disclosure provides methods and apparatus for evaluating tissue structure in damaged or healing tissue. The present disclosure also provides methods of identifying a patient at the onset of risk of pressure ulcer or at risk of the onset of pressure ulcer, and treating the patient with anatomy-specific clinical intervention selected based on specific ultrasonographic characteristics. The present disclosure also provides methods of stratifying groups of patients based on the risk of wound development, and methods of reducing the incidence or severity of tissue damage in patients admitted to a care facility. The present disclosure also provides methods of detecting tissue damage before the tissue damage is visible on a patient's skin.

BACKGROUND

The skin is the largest organ in the human body. It is readily exposed to different kinds of damages and injuries. Skin damage and injury may result when the skin and its surrounding tissues are unable to redistribute external pressure and mechanical forces, ulcers may be formed. Prolonged continuous exposure to even modest pressure, such as the pressure created by the body weight of a supine patient on their posterior skin surfaces, may lead to a pressure ulcer. In the presence of other damage, such as the neuropathy and peripheral tissue weakening that can be induced by diabetes, even periodic exposure to moderate levels of pressure and stress may lead to an ulcer, for example a foot ulcer.

Pressure ulcers are developed by approximately 2.5 million people a year in the United States and an equivalent number in the European Union. In long-term and critical-care settings, up to 25% of elderly and immobile patients develop pressure ulcers. Approximately 60,000 U.S. patients die per year due to infection and other complications from pressure ulcers.

Most pressure ulcers occur over bony prominences, where there is less tissue for compression and the pressure gradient within the vascular network is altered. Pressure ulcers are categorized in one of six stages, ranging from the earliest stage currently recognized, in which the skin remains intact but may appear red over a bony prominence (Stage 1), to a stage where tissue is broken and bone, tendon or muscle is exposed (Stage 4), to a deep tissue pressure injury stage showing non-blanchable deep red, maroon, or purple discoloration, and finally to a stage where there is obscured full-thickness skin and tissue loss (unstageable). Detecting pressure ulcers before the skin breaks and treating them to avoid progression to later stages is a goal of policy makers and care providers in major economies. Most pressure ulcers are preventable, and if identified before the first stage of ulceration, deterioration of the underlying tissue can be halted.

Detecting tissue damage before the skin breaks and intervening with the appropriate therapy to avoid further deterioration of the underlying tissue is desirable not only for the patient but society. The average cost of treating pressure-induced damage at the earliest visible sign (a Stage 1 ulcer) is only $2,000 but this rises to $129,000 when the ulcer is deep enough to expose muscle or bone (a Stage 4 ulcer). See, e.g., Brem, H. et al. (2010). High Cost of Stage IV Pressure Ulcers. *Am. J. Surg.* October; 200(4):473-477. Currently, patients normally receive universal prevention of pressure ulcers, meaning that the prevention does not target to any particular anatomical sites. Patients only receive a targeted, localized, treatment of ulcer after the pressure ulcer is developed to the point that it can be identified by a visual assessment. The current standard to detect pressure ulcers is by visual inspection, which is subjective, unreliable, untimely, and lacks specificity. See, e.g., Pancorbo-Hidalgo P. et al. (2006). Risk assessment scales for pressure ulcer prevention: a systematic review. *Journal of Advanced Nursing*, 54, 94-110; Garcia-Fernandez, F. P. (2014). Predictive Capacity of Risk Assessment Scales and Clinical Judgment for Pressure Ulcers: A Meta-analysis. *Journal of wound, Ostomy and Continence Nursing* 41, 24-34. Therefore, even when a patient is experiencing inflammation of the skin, a precursor of ulcer development, he or she would not be receiving a targeted, localized treatment for the developing ulcer. Instead, the inflammation would continue to develop into a full-blown ulcer.

Skin damage and injury may also result from certain types of surgical procedures, for example reconstructive surgery involving skin flaps, which sever blood vessels in or around the area of surgery. Healing of damaged or separated tissue is dependent upon re-establishment of adequate blood flow throughout the damaged area. Determining whether an area of tissue is healing, i.e. that blood flow through the tissue is increasing to a normal level, is difficult to do via visual inspection. Existing equipment can measure certain attributes, such as the oxygenation level of the blood, that are at best indirect measures of blood flow.

Ultrasound includes soundwaves having frequencies higher than the upper audible limit of human being. Ultrasound imaging, or medical sonography, employs frequencies from 20 kHz up to several gigahertz to provide non-invasive images, or sonographs, of tissue structures. An ultrasound imaging probe sends sound waves propagating through the skin of a patient, and the sound waves echo off tissues with different reflection properties, which are recorded and displayed as an image in real-time.

Unlike other common methods of imaging, ultrasound devices are portable and can be brought to the bedside. It also does not involve the use of harmful ionizing radiation. It is a convenient and cost-effective imaging modality. Trained professionals may evaluate and interpret sonographs obtained from ultrasound imaging.

SUMMARY

Systematic methods using non-invasive, objective measurements to identify the onset of the risk of pressure ulcer before visible skin damages, followed by administering individualized intervention at specific anatomy are provided. Systematic methods using non-invasive, objective measurements to identify the onset of a pressure ulcer before visible skin damages, followed by administering individualized intervention at specific anatomy are also provided. Methods for monitoring progression of wound healing and consistency of intervention compliance are further provided.

In an aspect, the present disclosure provides for, and includes, an apparatus for producing sonographic images of tissue below a patient's intact skin, comprising: an emitter configured to emit sound waves at an intermediate frequency of about 10 MHz when activated, a receiver configured to received returned sound waves vibrations, and convert the vibrations into electrical pulses, and a processor coupled to the receiver. In an aspect, the processor is configured to: receive electrical pulses from the receiver, determine the length of time for the sound waves to return, determine the intensity of the returned sound waves, and generate a sonography image. In an aspect, the apparatus further comprises a display configured to receive the sonography image and provide the sonography image on the display.

In an aspect, the present disclosure provides for, and includes, a method of assessing sonographic characteristics in a tissue below a patient's intact skin, the method comprising the steps of: emitting sound waves into the patient's skin at a first location, receiving a portion of the returned sound waves that have been echoed from the tissue, determining the length of time for the sound waves to return, determining the intensity of the returned sound waves, generating a sonography image, obtaining the sonography image, and obtaining the number and type of one or more sonographic characteristics. In an aspect, the one or more sonographic characteristics is selected from the group consisting of unclear layered structure, hypoechoic lesion, discontinuous fascia, and heterogeneous hypoechoic area.

In an aspect, the present disclosure provides for, and includes, a method for reducing the incidence of wound development in patients admitted to a care facility, the method comprising the steps of: evaluating a patient for a risk of tissue damage upon admission to the care facility, administering an intervention of level-0 if the number of sonographic characteristics present is below or equal to a first threshold, and administering an intervention of level-N if the number of sonographic characteristics present exceeds the first threshold, wherein N is an integer ≥1. In an aspect, evaluating comprises: obtaining a sonography image of the patient at one or more body locations at risk of wound development, and determining a number of sonographic characteristics of tissue damage present in the sonography image.

In an aspect, the sonographic characteristic is selected from the group consisting of unclear layered structure, hypoechoic lesion, discontinuous fascia, and heterogeneous hypoechoic area. In an aspect, the sonographic characteristic is unclear layered structure. In an aspect, the sonographic characteristic is hypoechoic lesion. In an aspect, the sonographic characteristic is discontinuous fascia. In an aspect, the sonographic characteristic is heterogeneous hypoechoic area. In an aspect, the wound is selected from the group consisting of a pressure ulcer, a diabetic foot ulcer, deep tissue injury, a vascular ulcer, and a burn wound.

In an aspect, the one or more body locations at risk of wound development is selected from the group consisting of a sternum, a sacrum, a heel, a scapula (os latum scapularum), an elbow, an ear, and other fleshy tissues over a bony prominence of a patient. In an aspect, the one or more body locations at risk of wound development comprises an anatomical site in long-term contact with a medical device. In an aspect, the one or more body locations at risk of wound development is selected from the group consisting of a cheek, a nose, a chest, a stomach, and a lower abdomen area.

In an aspect, the intervention of level-N is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

In an aspect, the present disclosure provides for, and includes, a method of stratifying a plurality of patients in a care facility based on care levels, the method comprising the steps of: obtaining a sonography image of a patient in the plurality of patients at one or more body locations selected for monitoring, determining whether a sonographic characteristic of tissue damage is present in the sonography image, determining a care level of N care levels that corresponds to the number and type of sonographic characteristic present, assigning the care level to the patient based on the previous step, and arranging the patient of the plurality of patients into groups based on the patient's assigned care levels.

In an aspect, the sonographic characteristic is selected from the group consisting of unclear layered structure, hypoechoic lesion, discontinuous fascia, and heterogeneous hypoechoic area. In an aspect, the sonographic characteristic is a discontinuous fascia. In an aspect, the one or more body locations is selected from the group consisting of a sternum, a sacrum, a heel, a scapula (os latum scapularum), an elbow, an ear, and other fleshy tissues over a bony prominence of a patient. In an aspect, the one or more body locations comprises an anatomical site in long-term contact with a medical device. In an aspect, the one or more body locations is selected from the group consisting of a cheek, a nose, a chest, a stomach, and a lower abdomen area. In an aspect, assigning a care level to the patient is based on the presence or absence of discontinuous fascia. In an aspect, assigning a care level to the patient is based on a change in the presence of unclear layered structure over a period of two weeks.

In an aspect, the present disclosure provides for, and includes, a method for identifying and providing an appropriate level of care to a patient in a care facility, the method comprising the steps of: obtaining a plurality of sonography images of the patient at one or more body locations, determining whether a sonographic characteristic of tissue damage is present in the plurality of sonography images, providing one or more anatomy-specific interventions based on the presence or absence of sonographic characteristics in the previous step, increasing the level of anatomy-specific interventions based on an increase in the number of sonographic characteristics, and decreasing the level of anatomy-specific interventions based on a decrease in the number of sonographic characteristics.

In an aspect, the sonographic characteristic is selected from the group consisting of unclear layered structure, hypoechoic lesion, discontinuous fascia, and heterogeneous hypoechoic area. In an aspect, the sonographic characteristic is a discontinuous fascia. In an aspect, the sonographic characteristic is unclear layered structure. In an aspect, the one or more body locations is selected from the group consisting of a sternum, a sacrum, a heel, a scapula (os latum scapularum), an elbow, an ear, and other fleshy tissues over a bony prominence of a patient. In an aspect, the one or more body locations comprises an anatomical site in long-term contact with a medical device. In an aspect, the one or more body locations is selected from the group consisting of a cheek, a nose, a chest, a stomach, and a lower abdomen area.

In an aspect, the anatomy-specific intervention is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface. In an aspect, the level of anatomy-specific interventions is increased if the number of sonographic characteristics exceeds a first threshold. In an aspect, the level of anatomy-specific interventions is decreased if the number of sonographic characteristics falls below a second threshold.

In an aspect, the present disclosure provides for, and includes, a method for assigning a patient in a care facility to a risk category selected from a plurality of risk categories, the method comprising the steps of: obtaining a plurality of initial sonography images of the patient at one or more body locations selected for monitoring, determining whether a sonographic characteristic is present in the plurality of sonography images, assigning the patient to a risk category selected from the plurality of risk categories wherein the assigning is based partially on the presence or absence of sonographic characteristics in the previous step.

In an aspect, the sonographic characteristic is selected from the group consisting of unclear layered structure, hypoechoic lesion, discontinuous fascia, and heterogeneous hypoechoic area. In an aspect, the sonographic characteristic is a discontinuous fascia. In an aspect, the sonographic characteristic is unclear layered structure. In an aspect, the one or more body locations selected for monitoring is selected from the group consisting of a sternum, a sacrum, a heel, a scapula (os latum scapularum), an elbow, an ear, and other fleshy tissues over a bony prominence of a patient. In an aspect, the one or more body locations selected for monitoring comprises an anatomical site in long-term contact with a medical device. In an aspect, the one or more body locations selected for monitoring is selected from the group consisting of a cheek, a nose, a chest, a stomach, and a lower abdomen area.

In an aspect, the present disclosure provides for, and includes, a method for managing care of a patient in a care facility, the method comprising the steps of: obtaining a plurality of first sonography images of the patient at one or more body locations selected for monitoring upon admission to a care facility, determining whether a sonographic characteristic is present in the plurality of first sonography images, setting an intervention level to N=1 if the number of sonographic characteristics present is above a first threshold, implementing a level-N intervention for each of the one or more body location having a number of sonographic characteristics present above the first threshold, obtaining a plurality of subsequent sonography images at each of the one or more body locations at a level-N frequency, and determining if new sonographic characteristics are present in the plurality of subsequent sonography images.

In an aspect, the sonographic characteristic is selected from the group consisting of unclear layered structure, hypoechoic lesion, discontinuous fascia, and heterogeneous hypoechoic area. In an aspect, the sonographic characteristic is a discontinuous fascia. In an aspect, the sonographic characteristic is unclear layered structure. In an aspect, the body location selected for monitoring is selected from the group consisting of a sternum, a sacrum, a heel, a scapula (os latum scapularum), an elbow, an ear, and other fleshy tissues over a bony prominence of a patient. In an aspect, the body location selected for monitoring comprises an anatomical site in long-term contact with a medical device. In an aspect, the body location selected for monitoring is selected from the group consisting of a cheek, a nose, a chest, a stomach, and a lower abdomen area.

In an aspect, the level-N intervention is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

In an aspect, the present disclosure provides for, and includes, a method of identifying and treating a patient at risk of tissue damage, the method comprising the steps of: evaluating a patient for a risk of tissue damage upon admission to a care facility, administering a first intervention of level-0 if the first number of sonographic characteristics present is below or equal to a first threshold, and administering a first intervention of level-N if the first number of sonographic characteristics present is above the first threshold, where N is an integer and N has a value of 1 or greater. In an aspect, the evaluating step comprises: obtaining a first plurality of sonography images in the patient, and determining a first number of sonographic characteristics present in the first plurality of sonography images.

In an aspect, the method further comprises the steps of: obtaining a second plurality of sonography images in the patient at a first pre-determined frequency corresponding to the administered intervention level, determining a second number of sonographic characteristics present in the second plurality of sonography images, determining whether the second number of sonographic characteristics exceeds a second threshold, continuing to administer the first intervention if the second number of sonographic characteristics present does not exceed the second threshold, continuing to take a plurality of sonography images at the first pre-determined frequency if the second number of sonographic characteristics present does not exceed the second threshold, administering a second intervention of level-M if the second number of sonographic characteristics present exceeds the second threshold, where M is an integer and M is greater than N, and obtaining a third plurality of sonography images at a pre-determined frequency corresponding to level-M if the second number of sonographic characteristics present exceeds the second threshold.

In an aspect, the method further comprises the steps of: determining whether the second number of sonographic characteristics present is below or equal to a third threshold, continuing to administer the first intervention if the second number of sonographic characteristics present is not less than a third threshold, continuing to take a plurality of sonography images at the first pre-determined frequency if the second number of sonographic characteristics present is not less than the third threshold, administering a third intervention of level-L if the second number of sonographic characteristics present is less than the third threshold and if the first intervention is not of level-0, where L is an integer and L is less than N, and obtaining a plurality of sonography images at a pre-determined frequency corresponding to level-L if the second number of sonographic characteristics present is less than a third threshold.

In an aspect, the first intervention of level-N is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface. In an aspect, the second intervention of level-M is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface. In an aspect, the third intervention of level-L is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

In an aspect, the sonographic characteristics are selected from the group consisting of unclear layered structure, hypoechoic lesion, discontinuous fascia, and heterogeneous hypoechoic area. In an aspect, the sonographic characteristic is a discontinuous fascia. In an aspect, the sonographic characteristic is unclear layered structure.

In an aspect, the first plurality of sonography images is obtained at or around one or more body locations selected from the group consisting of a sternum, a sacrum, a heel, a scapula (os latum scapularum), an elbow, an ear, and other fleshy tissues over a bony prominence of a patient. In an aspect, the first plurality of sonography images is obtained at or around an anatomical site in long-term contact with a medical device. In an aspect, the first plurality of sonography images is obtained at or around one or more body locations selected from the group consisting of a cheek, a nose, a chest, a stomach, and a lower abdomen area.

In an aspect, the present disclosure provides for, and includes, a method of slowing the progression of skin and tissue damage in a patient in need thereof, the method comprising the steps of: identifying a current intervention of level-K received by the patient, obtaining a plurality of sonography images in the patient, identifying a sonographic characteristic in the plurality of sonography images, determining a first number of sonographic characteristics present in the plurality of sonography images, continuing to administer the current intervention of level-K if the first number of sonographic characteristics is below or equal to a first threshold, continuing to take a plurality of sonography images at a pre-determined frequency corresponding to level-K if the first number of sonographic characteristics is below or equal to the first threshold, administering a new intervention of level-N if the number of sonographic characteristics exceeds the first threshold, where N has a value greater than K, and taking a plurality of sonography images at a pre-determined frequency corresponding to level-N if the number of sonographic characteristics exceeds the first threshold.

In an aspect, the method further comprises the steps of: determining whether the first number of sonographic characteristics present is less than a second threshold, administering an intervention of level-L if the first number of sonographic characteristics is less than a second threshold, where L has a non-negative value lesser than K, and obtaining a plurality of sonography images at a pre-determined frequency corresponding to level-L if the first number of sonographic characteristics is less than the second threshold.

In an aspect, the sonographic characteristic is selected from the group consisting of unclear layered structure, hypoechoic lesion, discontinuous fascia, and heterogeneous hypoechoic area. In an aspect, the sonographic characteristic is a discontinuous fascia. In an aspect, the sonographic characteristic is unclear layered structure. In an aspect, the sonographic characteristic is hypoechoic lesion. In an aspect, the sonographic characteristic is heterogeneous hypoechoic area.

In an aspect, the plurality of sonography images is obtained at or around one or more body locations selected from the group consisting of a sternum, a sacrum, a heel, a scapula (os latum scapularum), an elbow, an ear, and other fleshy tissues over a bony prominence of a patient. In an aspect, the plurality of sonography images is obtained at or around an anatomical site in long-term contact with a medical device. In an aspect, the plurality of sonography images is obtained at or around one or more body locations selected from the group consisting of a cheek, a nose, a chest, a stomach, and a lower abdomen area.

In an aspect, the present disclosure provides for, and includes, a method of identifying and treating a patient in need of an intervention, the method comprising the steps of: obtaining a plurality of sonography images at an anatomic site of the patient, identifying a sonographic characteristic in the plurality of sonography images, determining a number of sonographic characteristics from the plurality of sonography images, determining whether the number of sonographic characteristics exceeds a threshold corresponding to level-N, where N is greater than or equal to 2, administering the intervention to the anatomic site if the number of sonographic characteristics exceeds the threshold, and taking a plurality of sonography images every two hours if the number of sonographic characteristic exceeds the threshold.

In an aspect, the sonographic characteristic is selected from the group consisting of unclear layered structure, hypoechoic lesion, discontinuous fascia, and heterogeneous hypoechoic area. In an aspect, the sonographic characteristic is a hypoechoic lesion. In an aspect, the anatomical site is selected from the group consisting of a sternum, a sacrum, a heel, a scapula (os latum scapularum), an elbow, an ear, and other fleshy tissues over a bony prominence of a patient. In an aspect, the intervention is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

In an aspect, the present disclosure provides for, and includes, a method for identifying damaged tissue, the method comprising the steps of: obtaining a first sonography image from a first location on a patient's skin, obtaining a second sonography image from a second location that is bisymmetric relative to the first location, identifying sonographic characteristics in each of the first and second sonography images, determining the number of sonographic characteristics from each of the first and second sonography image, determining a difference in the number of sonographic characteristics between a first sonography image and a second sonography image, and determining that there is tissue damage at the first or second location if the difference in the number of sonographic characteristics between the first sonography image and the second sonography image exceeds a threshold value.

In an aspect, the sonographic characteristic is selected from the group consisting of unclear layered structure, hypoechoic lesion, discontinuous fascia, and heterogeneous hypoechoic area. In an aspect, the sonographic characteristic is a discontinuous fascia. In an aspect, the location is selected from the group consisting of a sternum, a sacrum, a heel, a scapula (os latum scapularum), an elbow, an ear, and other fleshy tissues over a bony prominence of a patient.

In an aspect, the present disclosure provides for, and includes, a method of detecting tissue damage before it is visible on a patient's skin, the method comprising the steps of: obtaining a plurality of sonography images at a single location at incremental times, identifying sonographic characteristics in each of the plurality of sonography images, determining the number of sonographic characteristics from each of the plurality of sonography images, calculating a slope between the latest number of sonographic characteristics and the immediately prior number of sonographic characteristics, comparing the slope to a threshold value, and determining that there is tissue damage if the slope exceeds the threshold value.

In an aspect, the sonographic characteristic is selected from the group consisting of unclear layered structure, hypoechoic lesion, discontinuous fascia, and heterogeneous hypoechoic area. In an aspect, the sonographic characteristic is a discontinuous fascia. In an aspect, the location is selected from the group consisting of a sternum, a sacrum, a heel, a scapula (os latum scapularum), an elbow, an ear, and other fleshy tissues over a bony prominence of a patient.

In an aspect, the present disclosure provides for, and includes, a method of detecting tissue damage before it is visible on a patient's skin, the method comprising the steps of: obtaining a plurality of sonography images at a single location at incremental times, identifying sonographic characteristics in each of the plurality of sonography images, determining the number of sonographic characteristics from each of the plurality of sonography images, calculating a difference value of the maximum number of sonographic characteristics and the minimum number of sonographic characteristics for each incremental time, calculating a derivative of the difference value with respect to time, comparing the derivative to a threshold value, and determining that there is tissue damage if the derivative exceeds the threshold value.

In an aspect, the sonographic characteristic is selected from the group consisting of unclear layered structure, hypoechoic lesion, discontinuous fascia, and heterogeneous hypoechoic area. In an aspect, the sonographic characteristic is a discontinuous fascia. In an aspect, the location is selected from the group consisting of a sternum, a sacrum, a heel, a scapula (os latum scapularum), an elbow, an ear, and other fleshy tissues over a bony prominence of a patient.

In an aspect, the present disclosure provides for, and includes, a method of detecting tissue damage before it is visible on a patient's skin, the method comprising the steps of:

obtaining a plurality of sonography images at a single location at incremental times, identifying sonographic characteristics in each of the plurality of sonography images, determining the number of sonographic characteristics from each of the plurality of sonography images, calculating a difference value of the maximum number of sonographic characteristics and the minimum number of sonographic characteristics for each incremental time, fitting a curve to a predetermined number of the most-recent difference values, calculating a curvature of the fitted curve, comparing the curvature to a threshold value, and determining that there is tissue damage if the curvature exceeds the threshold value.

In an aspect, the sonographic characteristic is selected from the group consisting of unclear layered structure, hypoechoic lesion, discontinuous fascia, and heterogeneous hypoechoic area. In an aspect, the sonographic characteristic is a discontinuous fascia. In an aspect, the location is selected from the group consisting of a sternum, a sacrum, a heel, a scapula (os latum scapularum), an elbow, an ear, and other fleshy tissues over a bony prominence of a patient.

BRIEF DESCRIPTION OF THE DRAWINGS

Aspects of the disclosure are herein described, by way of example only, with reference to the accompanying drawings.

With specific reference now to the drawings in detail, it is stressed that the particulars shown are by way of example and are for purposes of illustrative discussion of aspects of the disclosure. In this regard, the description and the drawings, considered alone and together, make apparent to those skilled in the art how aspects of the disclosure may be practiced.

DETAILED DESCRIPTION

Figure 1A:
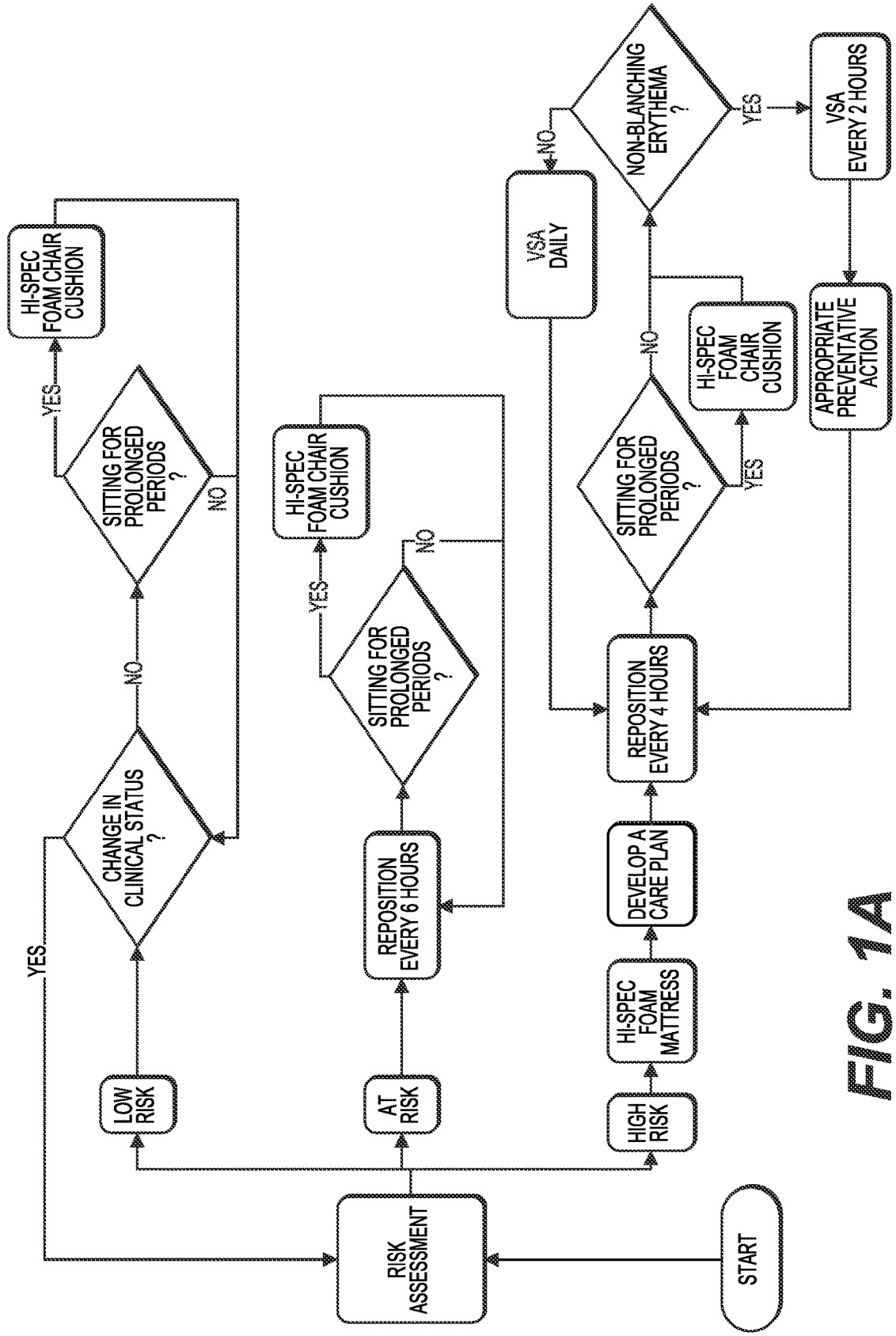
FIG. 1A is an example of a currently recommended treatment decision pathway for preventing pressure ulcers in hospital patients using a combination of risk assessment and visual assessment.

This description is not intended to be a detailed catalog of all the different ways in which the disclosure may be implemented, or all the features that may be added to the instant disclosure. For example, features illustrated with respect to one embodiment may be incorporated into other embodiment, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to effect a disavowal of any part of the full scope of the invention. Hence, the following descriptions are intended to illustrate some particular embodiments of the disclosure, and not to exhaustively specify all permutations, combinations and variations thereof.

Unless otherwise defined, all technical and scientific terms used herein have the same meaning as commonly understood by one of ordinary skill in the art to which this disclosure belongs. The terminology used in the description of the disclosure herein is for the purpose of describing particular aspects or embodiments only and is not intended to be limiting of the disclosure.

All publications, patent applications, patents and other references cited herein are incorporated by reference in their entireties for the teachings relevant to the sentence and/or paragraph in which the reference is presented. References to techniques employed herein are intended to refer to the techniques as commonly understood in the art, including variations on those techniques or substitutions of equivalent techniques that would be apparent to one of skill in the art.

Unless the context indicates otherwise, it is specifically intended that the various features of the disclosure described herein can be used in any combination. Moreover, the present disclosure also contemplates that in some embodiments of the disclosure, any feature or combination of features set forth herein can be excluded or omitted.

The methods disclosed herein include and comprise one or more steps or actions for achieving the described method. The method steps and/or actions may be interchanged with one another without departing from the scope of the present disclosure. In other words, unless a specific order of steps or actions is required for proper operation of the embodiment, the order and/or use of specific steps and/or actions may be modified without departing from the scope of the present disclosure.

As used in the description of the disclosure and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The terms "about" and "approximately" as used herein when referring to a measurable value such as a length, a frequency, or a measurement value and the like, is meant to encompass variations of ±20%, ±10%, ±5%, ±1%, ±0.5%, or even ±0.1% of the specified amount.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

As used herein, the term "exemplary" is used to mean serving as an example, instance, or illustration. Any embodiment or aspect described as "exemplary" is not necessarily to be construed as preferred or advantageous over other embodiments or aspects, nor is it meant to preclude equivalent structures and techniques known to those of ordinary skill in the art. Rather, use of the word exemplary is intended to present concepts in a concrete fashion, and the disclosed subject matter is not limited by such examples.

As used herein, the term "patient" comprises both human and animal subjects.

As used herein, the term "skin" indicates the surface of a patient's body.

As used herein, the term "tissue" refers to an ensemble of similar cells and their extracellular matrix from the same origin that together carry out a specific function. In some aspects, tissue includes a plurality of layers of the patient's body starting from the stratum corneum and including additional deeper structures such as the epidermis, the dermis, and a portion of deeper tissue that includes blood vessels. In an aspect, tissue does not include the stratum corneum.

As used herein, the term "wound" refers to damaged or injured tissue, which may or may not be visible on the surface of the skin. A wound may be open or closed. A wound may arise from a surgical procedure. A wound may be a burn wound. In an aspect, a wound is a pressure ulcer. In a further aspect, the pressure ulcer is subcutaneous. In one aspect, a pressure ulcer is a pressure ulcer resulting from an extended period of use of a medical device such as, for example, a mask, a tubing, or a strap. In an aspect, a wound is a diabetic foot ulcer. In an aspect, a wound is a vascular ulcer.

As used herein, "tissue biocapacitance" refers to a biophysical marker for detecting initial tissue damage based on the increased level of fluids that build up in the interstitial space. Without being bound by theory, the greater the fluid content in a tissue, the higher the biocapacitance value becomes. In some aspects, the methods described herein comprise a step of measuring the biocapacitance in a tissue. In some aspects, the methods described herein comprise a step of measuring the biocapacitance of the skin.

As used herein, the term "time delta" refers to a calculated difference between two values derived from measurements obtained at different time from a subject. In an aspect, each of the two values is an average value calculated from measurements obtained at approximately the same time. In an aspect, each of the two values is a summation value calculated from measurements obtained at approximately the same time. In an aspect, two measurements are obtained at approximately the same time when they are taken no more than about 10 hours apart, no more than about 8 hours apart, no more than about 6 hours, no more than about 5 hours apart, no more than about 4 hours apart, no more than about 3 hours apart, no more than about 2 hours apart, or no more than about 1 hour apart.

As used herein, the variables "K," "L," "M," and "N" are non-negative integers.

As used herein, the term "anatomy-specific" refers to the application of clinical interventions to the same locations where certain sonography images are taken.

As used herein, a "system" may be a collection of devices in wired or wireless communication with each other.

As used herein, "bisymmetric" refers to a pair of locations that are approximately equidistant from a line of symmetry.

As used herein, the terms "sonography," "ultrasonography," "ultrasound scanner," "ultrasound device," "ultrasound imager," or "scanner," comprises any method or device that produces images using sound waves. In an aspect, an ultrasound scanner can produce images that are 2-dimensional. In an aspect, an ultrasound scanner can produce images that are 3-dimensional. In an aspect, the ultrasound scanner emits and collects pulsed sound waves. In an aspect, the ultrasound scanner emits and collects continuous sound waves. In an aspect, the ultrasound scanner is portable. In an aspect, the ultrasound scanner is hand-held. In an aspect, the ultrasound scanner comprises a probe. In an aspect, the ultrasound scanner comprises a transducer. In an aspect, the ultrasound scanner comprises a display configured to show the image obtained.

As used herein, the term "sound waves" means energy that propagates as acoustic waves, having a frequency of 20 kHz or higher. Without being bound by theory, the resolution of features in the ultrasound image depends on the wavelength (or frequency) of the sound waves emitted by the ultrasound device. In an aspect, the ultrasound device uses sound waves of greater than 20 kHz. In an aspect, the ultrasound device uses sound waves of greater than 20 kHz. In an aspect, the ultrasound device uses sound waves of greater than 2 MHz. In an aspect, the ultrasound device uses sound waves of greater than 3 GHz.

Within this document, identification of sound as having a certain wavelength has the same meaning as identifying the sound as having a certain frequency, as the wavelength and frequency of sound are uniquely related. Reference to a frequency of sound is considered equivalent and interchangeable with a reference to the wavelength of the same sound.

As used herein, the term "method" comprises a sequence of activities, e.g. steps. In certain embodiments, the steps must be performed in a particular order while, in other embodiments, the sequence of activities may be interchanged. A "method" is considered equivalent to and interchangeable with a "process." In certain embodiments, one or more disclosed steps are omitted.

Apparatus and Method for Sonographic Imaging and Assessing Sonographic Characteristics In an aspect, the present disclosure provides an apparatus for producing sonographic images of tissue below a patient's intact skin, comprising: an emitter configured to emit sound waves at an intermediate frequency of about 10 MHz when activated, a receiver configured to received returned sound waves vibrations, and convert the vibrations into electrical pulses, and a processor coupled to the receiver, where the processor is configured to receive electrical pulses from the receiver, determine the length of time for the sound waves to return, determine the intensity of the returned sound waves, and generate a sonography image. In an aspect, the apparatus further comprises a display configured to receive the sonography image and provide the sonography image on the display.

In an aspect, the present disclosure provides a method for assessing sonographic characteristics in a tissue below a patient's intact skin, the method comprising the steps of: emitting sound waves into the patient's skin at a first location, receiving a portion of the returned sound waves that have been echoed from the tissue, determining the length of time for the sound waves to return, determining the intensity of the returned sound waves, generating a sonography image, obtaining the sonography image, and obtaining the number and type of one or more sonographic characteristics.

In an aspect, the one or more sonographic characteristics is selected from the group consisting of unclear layered structure, hypoechoic lesion, discontinuous fascia, and heterogeneous hypoechoic area. Without being bound by theory, deep tissue injury related to pressure ulcers may be visualized by sonography. See, e.g., Aoi et al., *Plast. Reconstr. Surg.*, 124(2):540-50 (2009). Deep tissue injuries are characterized by four types of abnormal signs unique to ultrasonography: unclear layered structure, hypoechoic lesion, discontinuous fascia, and heterogeneous hypoechoic area. In an aspect, an unclear layered structure does not show a clear, layered structure in a sonogram, such as a subcutaneous fatty layer, superficial fascia, deep fascia, muscular layer, bursa, and bone. In an aspect, an unclear layered structure is a foggy-appearing area in a sonogram with low contrast and rough resolution. In an aspect, a hypoechoic lesion is tissue in the body that is more dense or solid than normal tissue, as visualized by sonography. In an aspect, a hypoechoic lesion is less echogenic, and appears darker than surrounding tissue in a sonogram. In an aspect, a discontinuous fascia is an interrupted high-signal line on a sonogram, corresponding to the superficial or deep fascia. In an aspect, a heterogeneous hypoechoic area has a diffuse border in a sonogram.

In an aspect, a sonography scan includes obtaining a sonography image at a single location on the patient's skin. In an aspect, a sonography scan includes obtaining a sonography image at multiple locations on the patient's skin. In an aspect, a sonography scan includes obtaining a plurality of sonography images at multiple locations on the patient's skin. In an aspect, evaluating a patient comprises obtaining a sonography image of the patient at one or more body locations. In an aspect, evaluating a patient comprises determining a number of sonographic characteristics present in a sonography image. In an aspect, evaluating a patient comprises determining a number of sonographic characteristics present in a plurality of sonography images.

In an aspect, an average number of sonographic characteristics at a location is obtained from two, three, four, five, six, seven, eight, nine, ten, or more than ten sonography images obtained at that location. In one aspect, a first difference in the number of sonographic characteristics is determined by the difference between the number of sonographic characteristics derived from measurements taken at two bisymmetric locations with respect to a centerline.

In an aspect, a number of sonographic characteristics may be determined from a plurality of sonography images made at a certain location, or in close proximity around a specific location, in a plurality of methods disclosed herein. In an aspect, a plurality of sonography images are made in a pre-determined pattern on the skin. In an aspect, a plurality of sonography images are made in a pre-determined pattern on the skin and the number of sonographic characteristics is determined from the sonography images obtained at pre-determined positions within the pattern. In an aspect, the number of sonographic characteristics is determined from a portion or subset of the plurality of sonography images obtained. In an aspect, the number of sonographic characteristics at a location is the average number of sonographic characteristics in the plurality of images obtained at that location. In an aspect, the number of sonographic characteristics at a location is the maximum number of sonographic characteristics in the plurality of images obtained at that location. In an aspect, the number of sonographic characteristics at a location is the median number of sonographic characteristics in the plurality of images obtained at that location. In an aspect, the number of sonographic characteristics at a location is the mode number of sonographic characteristics in the plurality of images obtained at that location.

Method for Reducing the Incidence of Wound Development Using Sonographic Characteristics In an aspect, the present disclosure provides a method for reducing the incidence of wound development in patients admitted to a care facility, the method comprising the steps of: evaluating a patient for a risk of tissue damage upon admission to the care facility, administering an intervention of level-0 if the number of sonographic characteristics present is below or equal to a first threshold, and administering an intervention of level-N if the number of sonographic characteristics present exceeds the first threshold, wherein N is an integer ≥1, and wherein evaluating comprises obtaining a sonography image of the patient at one or more body locations at risk of wound development, and determining a number of sonographic characteristics of tissue damage present in the sonography image.

In an aspect, a wound is a pressure ulcer. In one aspect, a pressure ulcer is a pressure ulcer resulting from an extended period of use of a medical device such as, for example, a mask, a tubing, or a strap. In an aspect, a wound is a diabetic foot ulcer. In an aspect, a wound is a vascular ulcer. In an aspect, a wound is a burn wound.

In an aspect, the incidence of ulcers in patients in the care facility is reduced to less than 1 in 100, less than 1 in 200, less than 1 in 300, less than 1 in 400, less than 1 in 500, less than 1 in 600, less than 1 in 700, less than 1 in 800, less than 1 in 900, or less than 1 in 1000.

In an aspect, a care facility is selected from the group consisting of a hospital, a recovery facility, an assisted living facility, a residential care facility, a nursing home, a long-term care facility, a continuing care community, and an independent living community. In an aspect, a care facility may be a home or other residence of the patient, whereupon the "admit" step will be a first evaluation of a patient at their home by a nurse or other caregiver. In one aspect, the schedule of interventions and evaluation intervals used in a home setting may be different than the corresponding interventions and intervals used at a hospital.

In an aspect, the methods disclosed herein comprise evaluating a newly admitted patient for a risk of tissue damage. In an aspect, evaluating a patient comprises performing a visual assessment. In one aspect, the visual assessment is performed in accordance with the guidelines of the National Pressure Ulcer Advisory Panel (NPUAP).

In one aspect, evaluating a patient comprises performing a risk assessment. In an aspect, the risk assessment is performed in accordance with a test selected from the group consisting of the Braden Scale, the Gosnell Scale, the Norton Scale, and the Waterlow Scale. In an aspect, evaluating a patient further comprises performing an assessment using one or more objective measurements selected from the group consisting of: sub-epidermal moisture, bioimpedance, blood perfusion, biocapacitance, blood oxygenation, pressure measurement; capillary pressure, magnetic resonance imaging, PET imaging, thermal imaging, spectral imaging, transcutaneous water loss, and detection of interleukin-1 alpha presence at one or more anatomic site of interest.

FIGS. 7A-D illustrate locations of tissue injury risk in circles for patients in different positions. In an aspect, one or more body locations at risk of developing pressure injuries is selected from the group consisting of the back of the head, shoulder, base of spine, buttocks, heel, toes, elbow, ear, hip, thigh, leg, rib cage, and knees. In an aspect, one or more body locations at risk of developing tissue injury is selected from the group consisting of sternum, a sacrum, a heel, a scapula (os latum scapularum), an elbow, an ear, and other fleshy tissues over a bony prominence of a patient.

In an aspect, a newly admitted patient receives an intake evaluation that includes one or more of a visual examination of a portion of the patient's skin, completion of at least a portion of a risk assessment protocol that evaluates one or more of nutrition, mobility, physical activity, physical strength, and ability to communicate, and sonography images are taken in one or more locations on the patient's skin. In an aspect, a sonography scan may include obtaining a plurality of sonography images at a single "location" on the patient's skin. In one aspect, "location" is considered as an area rather than a single point such that sonography images may be made at spatially separated points within the location. For example, a "heel" location includes the medial, lateral, and posterior surfaces around the heel as well as the posterior portion of the sole of that foot. In an aspect, a sonography scan includes obtaining a sonography image at a single location on the patient's skin. In an aspect, a sonography scan includes obtaining a sonography image at multiple locations on the patient's skin. In an aspect, a sonography scan includes obtaining a plurality of sonography images at multiple locations on the patient's skin. In an aspect, evaluating a patient comprises determining a number of sonographic characteristics in a sonography image. In an aspect, evaluating a patient comprises determining an average number of sonographic characteristics in a plurality of sonography images.

In one aspect, once the evaluation step is complete, a determination is made as to whether the patient's readings are abnormal, i.e., whether the combination of the results of the various elements of the evaluation indicate that the patient has, or is at risk of developing, further wound tissue damage. Each element of the evaluation may have an individual criterion for level of risk, for example a scoring system with threshold value that indicates an unacceptable risk. In an aspect, there is a protocol to combine the criteria to generate a composite parameter that can be used to select a level of intervention.

In an aspect, an intervention of level-0 is administered if the number of sonographic characteristics present is below or equal to a first threshold. In an aspect, an intervention of level-N is administered if the number of sonographic characteristics present is above a first threshold. In an aspect, a first threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a threshold can be scaled by a factor or a multiple based on the values provided herein. It will be understood that a threshold is not limited by design, but rather, one of ordinary skill in the art would be capable of choosing a predetermined value. In one aspect, thresholds of the present disclosure are varied according to the specific portion of a patient's body on which measurements are being made, or one or more characteristics of the patient such as age, height, weight, family history, ethnic group, and other physical characteristics or medical conditions.

In an aspect, if the patient is determined to be at an acceptable level of risk, the lowest level of intervention is implemented, designated herein as "level-zero" or "level-0", and the patient will be re-assessed using at least the sonography imaging protocol at a frequency, or conversely a time interval, associated with level-0. In an aspect, a level-0 intervention is administered if the number of sonographic characteristics present is below or equal to a threshold.

In an aspect, a number of sonographic characteristics above a first threshold value is an indication of a patient at risk of developing a pressure ulcer or tissue damage.

In one aspect, if the patient is determined to have abnormal readings, then a higher level of intervention is implemented. In an aspect, there is a defined hierarchy of intervention levels, with each level implementing a more intensive intervention than the next-lower level. In an aspect, each level also has a defined monitoring interval or frequency indicating how often a set of sonography images should be made, where higher levels will generally have shorter intervals. In an aspect, the process has been defined by the hospital, or other administering organization, to step up one level to a level-1 intervention at this point. In another aspect, a level-2 or higher level of intervention can be implemented. The process now enters a new loop where the patient will now be monitored at a level-N frequency where N is in the range of 1 to n, n being the highest defined level of intervention and monitoring.

In an aspect, a level-N intervention is administered if the number of sonographic characteristics is above a threshold. In an aspect, the level-N intervention is anatomy-specific.

In an aspect, sonography images of a body location identified as having possible damage in the initial set of sonography images are obtained at a first time interval. In an aspect, sonography images of all other body locations selected for monitoring are obtained at a second time interval that is longer than the first time interval. In an aspect, the values of the first and second time intervals are different depending on the risk category to which the patient has been assigned. For example, a high-risk patient will have a first time interval of 4 hours and a second time interval of 1 day while an at-risk patient will have a first time interval of 1 day and a second time interval of 1 week. In an aspect, the time interval may be event-based, for example upon a change of attending staff or shift change, rather than strictly based on time. In general, body locations that have a higher number of sonographic characteristics are scanned more often than other body locations that are monitored but having few (or none) sonographic characteristics in previous sonography imaging session.

In an aspect, the interval at which sonography images are taken is determined by the number of sonographic characteristics from the prior sonography imaging session. For example, a body location that had a number of sonographic characteristics greater than or equal to a first threshold in a previous imaging session is performed at a first time interval, while a sonography imaging is performed at a second time interval that is shorter than the first time interval when the prior number of sonographic characteristics at a body location was greater than or equal to a second threshold that is higher than the first threshold.

Methods of Assigning a Patient to a Risk Category

In an aspect, the present disclosure provides a method for assigning a patient in a care facility to a risk category selected from a plurality of risk categories, the method comprising the steps of: obtaining a plurality of initial sonography images of the patient at one or more body locations selected for monitoring, determining whether a sonographic characteristic is present in the plurality of sonography images, and assigning the patient to a risk category selected from the plurality of risk categories wherein the assigning is based partially on the presence or absence of sonographic characteristics in the previous step.

In one aspect, the risk level of the patient is determined entirely by sonographic imaging. In one aspect, the risk level of the patient is determined entirely by visual examination of the patient. In one aspect, the risk level of the patient is determined entirely by performing a risk assessment protocol on the patient. In one aspect, the risk level of the patient is determined by sonographic imaging and visual examination of the patient. In one aspect, the risk level of the patient is determined by performing a risk assessment protocol on the patient and a visual examination of the patient. In one aspect, the risk level of the patient is determined by sonographic imaging and performing a risk assessment protocol on the patient. In one aspect, the risk level of the patient is determined by sonographic imaging, performing a risk assessment protocol on the patient and a visual examination of the patient. In an aspect, there is a protocol to combine the criteria to generate a composite parameter that can be used to select a level of intervention.

In an aspect, the patient is assigned to a risk category selected from a plurality of risk categories. In an aspect, the risk categories comprise at-risk and high-risk categories. In an aspect, the risk categories comprise low-risk, and high-risk categories. In an aspect, the risk categories comprise low-risk, at-risk, and high-risk categories. In an aspect, there are 1, 2, 3, 4, 5, 6, 7, 8, 9, or 10 risk categories. In an aspect, a risk category is associated with a corresponding level of care. In an aspect, a risk category is associated with a corresponding level of intervention. In an aspect, a risk category is associated with a corresponding frequency of subsequent sonographic imaging.

In an aspect, the patient is assigned to a risk category based on the number of sonographic characteristics. In an aspect, the patient is assigned to a risk category by comparing the number of sonographic characteristics to a threshold value. In an aspect, the patient is assigned to a risk category by comparing the number of sonographic characteristics to a maximum number of sonographic characteristics. In an aspect, the assignment is based solely on the largest initial number of sonographic characteristics found during the initial sonography imaging scan.

Methods of Assigning Patients to Care Levels and Intervention Levels

In an aspect, the present disclosure provides a method of stratifying a plurality of patients in a care facility based on care levels, the method comprising the steps of: obtaining a sonography image of a patient in the plurality of patients at one or more body locations selected for monitoring, determining whether a sonographic characteristic of tissue damage is present in the sonography image, determining a care level of N care levels that corresponds to the number and type of sonographic characteristic present, assigning the care level to the patient based on the previous step, and arranging the patient of the plurality of patients into groups based on the patient's assigned care levels.

In an aspect, the patient is assigned to a care level based on the number of sonographic characteristics. In an aspect, the patient is assigned to a care level of N care levels that corresponds to the number of sonographic characteristics. In an aspect, there are 1, 2, 3, 4, 5, 6, 7, 8, 9, or 10 care levels. In an aspect, each of the N care levels corresponds to a range of numbers of sonographic characteristics. In an aspect, a care level is associated with a corresponding level of intervention. In an aspect, a care level is associated with a corresponding frequency of subsequent sonographic imaging. In an aspect, a plurality of patients are grouped and arranged according to their assigned care levels. In an aspect, a plurality of patients are grouped such that patients within a group are assigned to the same care level. In an aspect, a plurality of patients are grouped such that patients within a group are given the same interventions.

In one aspect, the present disclosure provides a method for identifying and providing an appropriate level of care to a patient in a care facility, the method comprising the steps of: obtaining a plurality of sonography images of the patient at one or more body locations, determining whether a sonographic characteristic of tissue damage is present in the plurality of sonography images, providing one or more anatomy-specific interventions based on the presence or absence of sonographic characteristics in the previous step, increasing the level of anatomy-specific interventions based on an increase in the number of sonographic characteristics, and decreasing the level of anatomy-specific interventions based on a decrease in the number of sonographic characteristics.

In an aspect, the patient is assigned to a care level based on the number of sonographic characteristics. In an aspect, the patient is assigned to a care level of N care levels that corresponds to the number of sonographic characteristics. In an aspect, there are 1, 2, 3, 4, 5, 6, 7, 8, 9, or 10 care levels. In an aspect, each of the N care levels corresponds to a range of numbers of sonographic characteristics. In an aspect, a care level is associated with a corresponding level of intervention. In an aspect, a care level is associated with a corresponding frequency of subsequent sonographic imaging.

In an aspect, the patient's history is evaluated to determine whether their condition is improving. If the patient's condition is improving, for example as evidenced by a decreasing number of sonographic characteristics present, then the an intervention level is decreased. In an aspect, the current level of intervention continues to be implemented until the number of sonographic characteristics drops below the threshold. In an aspect, the level of intervention may be reduced based on the magnitude of the number of sonographic characteristics as the number of sonographic characteristics trends downward. If the patient's condition is worsening, for example as evidenced by an increasing number of sonographic characteristics, then the intervention level is increased. In an aspect, the current level of intervention continues to be implemented until the number of sonographic characteristics rises above the threshold. In an aspect, the level of intervention may be increased based on the magnitude of the number of sonographic characteristics as the number of sonographic characteristics trends upward.

In one aspect, if the patient does not show improvement, the process branches to an increase in the level of intervention provided that the skin is not broken, i.e., an open wound has not developed. If an open wound has developed, sonography imaging will now be made around the periphery of the open wound to map inflammation or other precursor indication of the wound enlarging. The open wound itself is treated and its periphery monitored until the wound closes.

In an aspect, an anatomy-specific intervention is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

In an aspect, the decision to implement an intervention for a particular body site, or a general intervention such as a high-spec mattress, is based on the number of sonographic characteristics found for that site in the sonography imaging scan. If the number of sonographic characteristics is less than a predetermined threshold, no intervention is required. If the number of sonographic characteristics is greater than the predetermined threshold, then an intervention is selected and implemented based partially on the body location and partially on the number of sonographic characteristics for that body location. The predetermined threshold for whether or not to select and implement an intervention may be higher or lower than the threshold for determination that there is possible damage at the body location.

Methods of Managing Care

In an aspect, the present disclosure provides for, and includes, a method for managing care of a patient in a care facility, the method comprising the steps of: obtaining a plurality of first sonography images of the patient at one or more body locations selected for monitoring upon admission to a care facility, determining whether a sonographic characteristic is present in the plurality of first sonography images, setting an intervention level to N=1 if the number of sonographic characteristics present is above a first threshold, implementing a level-N intervention for each of the one or more body location having a number of sonographic characteristics present above the first threshold, obtaining a plurality of subsequent sonography images at each of the one or more body locations at a level-N frequency, and determining if new sonographic characteristics are present in the plurality of subsequent sonography images.

In an aspect, a first threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a first threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a first threshold can be scaled by a factor or a multiple based on the values provided herein. It will be understood that a threshold is not limited by design, but rather, one of ordinary skill in the art would be capable of choosing a predetermined value based on a given unit of sonographic characteristic. In one aspect, thresholds of the present disclosure are varied according to the specific portion of a patient's body on which measurements are being made, or one or more characteristics of the patient such as age, height, weight, family history, ethnic group, and other physical characteristics or medical conditions.

In an aspect, N ranges from 1 to 50, such as from 1 to 2, from 1 to 3, from 1 to 4, from 1 to 5, from 1 to 6, from 1 to 7, from 1 to 8, from 1 to 9, from 1 to 10, from 1 to 15, from 1 to 20, from 1 to 25, from 1 to 30, from 1 to 35, from 1 to 40, or from 1 to 45. In one aspect, N is determined by the amount by which the number of sonographic characteristics exceeds the first threshold. In one aspect, a level-N intervention corresponds to a range of numbers of sonographic characteristics. In an aspect, a level-N intervention is associated with a corresponding anatomy-specific intervention. In an aspect, a level-N intervention is associated with a corresponding frequency of subsequent sonography imaging. In an aspect, the level-N intervention is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

In an aspect, care of a patient is discharge or transfer from the care facility. In an aspect, the condition of the patient upon discharge or transfer is documented. In an aspect, a final set of sonography images at one or more locations on the patient's body is taken before discharge or transfer. In one aspect, a final set of sonography images at one or more locations on the patient's body is made. In an aspect, these locations are one or more body locations selected for monitoring. In an aspect, these locations include areas that were not receiving an intervention and were not previously identified as at risk. In an aspect, this information is provided to the receiving caregiver.

Methods of Identifying and Treating a Patient at Risk of Tissue Damage

FIGS. 7A-D illustrate locations of tissue injury risk in circles for patients in different positions. In an aspect, a first plurality of sonography images is taken at or around one or more body locations selected from the group consisting of sternum, a sacrum, a heel, a scapula (os latum scapularum), an elbow, an ear, and other fleshy tissues over a bony prominence of a patient. In an aspect, a first plurality of sonography images is taken at and around one or more anatomical sites in long-term contact with a medical device, an anatomical site is selected from the group consisting of a cheek, a nose, a chest, a stomach, and a lower abdomen area. In an aspect, a first plurality of sonography images is separated into sub-groups for analysis based on the general location at which a measurement is taken. In an aspect, the number of sonographic characteristics is determined from a subset of the first plurality of sonography images. In one aspect, a first plurality of sonography images is taken at locations located on one or more concentric circles centered around an anatomical site. In an aspect, a first plurality of sonography images is taken at locations located on a straight line at approximately equidistance from an anatomical site.

In an aspect, a number of sonographic characteristics may be determined from a plurality of sonography images made at a certain location, or in close proximity around a specific location, in a plurality of methods disclosed herein. In an aspect, a plurality of sonography images are made in a pre-determined pattern on the skin. In an aspect, a plurality of sonography images are made in a pre-determined pattern on the skin and the number of sonographic characteristics is determined from the plurality of sonography images obtained at pre-determined positions within the pattern. In an aspect, the number of sonographic characteristics is determined from a portion or subset of the plurality of sonography images obtained. In an aspect, the number of sonographic characteristics at a location is the average number of sonographic characteristics in the plurality of images obtained at that location. In an aspect, the number of sonographic characteristics at a location is the maximum number of sonographic characteristics in the plurality of images obtained at that location. In an aspect, the number of sonographic characteristics at a location is the median number of sonographic characteristics in the plurality of images obtained at that location. In an aspect, the number of sonographic characteristics at a location is the mode number of sonographic characteristics in the plurality of images obtained at that location.

In an aspect, N ranges from 1 to 50, such as from 1 to 2, from 1 to 3, from 1 to 4, from 1 to 5, from 1 to 6, from 1 to 7, from 1 to 8, from 1 to 9, from 1 to 10, from 1 to 15, from 1 to 20, from 1 to 25, from 1 to 30, from 1 to 35, from 1 to 40, or from 1 to 45.

In one aspect, N is determined by the amount by which the first number of sonographic characteristic exceeds the first threshold. In an aspect, the amount by which a threshold established for (N+1) exceeds the first threshold is greater than the amount by which a threshold established for N exceeds the first threshold. In one aspect, the amount by which a threshold established for (N−1) exceeds the first threshold is less than the amount by which a threshold established for N exceeds the first threshold. In an aspect, the value of threshold established for (N+1) is greater than the value of the threshold established for N. In an aspect, the value of threshold established for N is greater than the value of the threshold established for (N−1).

Selection of Intervention Levels

In an aspect, a level-1 (N=1) intervention is applied to a patient having a number of sonographic characteristics exceeding the threshold by not more than 100% of the threshold value, such as not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-1 intervention is applied to a location at which a measurement was made.

In an aspect, a level-2 (N=2) intervention is applied to a patient having a number of sonographic characteristics exceeding the threshold by not more than 150% of the threshold value, such as not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-2 intervention is applied to a location at which a measurement was made.

In one aspect, a level-3 (N=3) intervention is applied to a patient having a number of sonographic characteristics exceeding the threshold by not more than 200% of the threshold value, such as not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-3 intervention is applied to a location at which a measurement was made.

In one aspect, a level-4 (N=4) intervention is applied to a patient having a number of sonographic characteristics exceeding the threshold by not more than 250% of the threshold value, such as not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-4 intervention is applied to a location at which a measurement was made.

In one aspect, a level-5 (N=5) intervention is applied to a patient having a number of sonographic characteristics exceeding the threshold by not more than 300% of the threshold value, such as not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-5 intervention is applied to a location at which a measurement was made.

In one aspect, a level-6 (N=6) intervention is applied to a patient having a number of sonographic characteristics exceeding the threshold by not more than 350% of the threshold value, such as not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-6 intervention is applied to a location at which a measurement was made.

In one aspect, a level-7 (N=7) intervention is applied to a patient having a number of sonographic characteristics exceeding the threshold by not more than 400% of the threshold value, such as not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-7 intervention is applied to a location at which a measurement was made.

In one aspect, a level-8 (N=8) intervention is applied to a patient having a number of sonographic characteristics exceeding the threshold by not more than 450% of the threshold value, such as not more than 445%, not more than 440%, not more than 435%, not more than 430%, not more than 425%, not more than 420%, not more than 415%, not more than 410%, not more than 405%, not more than 400%, not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-8 intervention is applied to a location at which a measurement was made.

In one aspect, a level-9 (N=9) intervention is applied to a patient having a number of sonographic characteristics exceeding the threshold by not more than 500% of the threshold value, such as not more than 495%, not more than 490%, not more than 485%, not more than 480%, not more than 475%, not more than 470%, not more than 465%, not more than 460%, not more than 455%, not more than 450%, not more than 445%, not more than 440%, not more than 435%, not more than 430%, not more than 425%, not more than 420%, not more than 415%, not more than 410%, not more than 405%, not more than 400%, not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-9 intervention is applied to a location at which a measurement was made.

In one aspect, a level-10 (N=10) intervention is applied to a patient having a number of sonographic characteristics exceeding the threshold by not more than 550% of the threshold value, such as not more than 545%, not more than 540%, not more than 535%, not more than 530%, not more than 525%, not more than 520%, not more than 515%, not more than 510%, not more than 505%, not more than 500%, not more than 495%, not more than 490%, not more than 485%, not more than 480%, not more than 475%, not more than 470%, not more than 465%, not more than 460%, not more than 455%, not more than 450%, not more than 445%, not more than 440%, not more than 435%, not more than 430%, not more than 425%, not more than 420%, not more than 415%, not more than 410%, not more than 405%, not more than 400%, not more than 395%, not more than 390%, not more than 385%, not more than 380%, not more than 375%, not more than 370%, not more than 365%, not more than 360%, not more than 355%, not more than 350%, not more than 345%, not more than 340%, not more than 335%, not more than 330%, not more than 325%, not more than 320%, not more than 315%, not more than 310%, not more than 305%, not more than 300%, not more than 295%, not more than 290%, not more than 285%, not more than 280%, not more than 275%, not more than 270%, not more than 265%, not more than 260%, not more than 255%, not more than 250%, not more than 245%, not more than 240%, not more than 235%, not more than 230%, not more than 225%, not more than 220%, not more than 215%, not more than 210%, not more than 205%, not more than 200%, not more than 195%, not more than 190%, not more than 185%, not more than 180%, not more than 175%, not more than 170%, not more than 165%, not more than 160%, not more than 155%, not more than 150%, not more than 145%, not more than 140%, not more than 135%, not more than 130%, not more than 125%, not more than 120%, not more than 115%, not more than 110%, not more than 100%, not more than 95%, not more than 90%, not more than 85%, not more than 80%, not more than 75%, not more than 70%, not more than 65%, not more than 60%, not more than 55%, not more than 50%, not more than 45%, not more than 40%, not more than 35%, not more than 30%, not more than 25%, not more than 20%, not more than 15%, not more than 10%, or not more than 5% of the threshold value. In an aspect, a level-10 intervention is applied to a location at which a measurement was made.

In one aspect, a level-N intervention is more intensive than a level-0 intervention. In an aspect, a level-(N+1) intervention is more intensive than a level-N intervention. In one aspect, a level-(N−1) intervention is less intensive than a level-N intervention.

Methods of Identifying and Treating a Patient at Risk of Tissue Damage—Subsequent Imaging In an aspect, the present disclosure further provides for, and includes, obtaining a second plurality of sonography images in the patient at a first pre-determined frequency corresponding to the administered intervention level, determining a second number of sonographic characteristics present in the second plurality of sonography images, determining whether the second number of sonographic characteristics exceeds a second threshold, continuing to administer the first intervention if the second number of sonographic characteristics present does not exceed the second threshold, continuing to take a plurality of sonography images at the first pre-determined frequency if the second number of sonographic characteristics present does not exceed the second threshold, administering a second intervention of level-M if the second number of sonographic characteristics present exceeds the second threshold, where M is an integer and M is greater than N, and obtaining a third plurality of sonography images at a pre-determined frequency corresponding to level-M if the second number of sonographic characteristics present exceeds the second threshold.

In one aspect, a pre-determined frequency is selected from the group consisting of at least once every 72 hours, at least once every 48 hours, at least once every 24 hours, at least once every 12 hours, at least once every 8 hours, at least once every 6 hours, at least once every 4 hours, at least once every 3 hours, at least once every 2 hours, at least once every hour, and at least once every half an hour.

In an aspect, a second plurality of sonography images is taken at or around one or more body locations selected from the group consisting of sternum, a sacrum, a heel, a scapula (os latum scapularum), an elbow, an ear, and other fleshy tissues over a bony prominence of a patient. In an aspect, a second plurality of sonography images is taken at and around one or more anatomical sites in long-term contact with a medical device, an anatomical site is selected from the group consisting of a cheek, a nose, a chest, a stomach, and a lower abdomen area. In an aspect, a second plurality of sonography images is separated into sub-groups for analysis based on the general location at which a measurement is taken. In an aspect, the second number of sonographic characteristics is determined from a subset of the second plurality of sonography images. In one aspect, a second plurality of sonography images is taken at locations located on one or more concentric circles centered around an anatomical site. In an aspect, a second plurality of sonography images is taken at locations located on a straight line at approximately equidistance from an anatomical site.

In an aspect, a second number of sonographic characteristics may be determined from a second plurality of sonography images made at a certain location, or in close proximity around a specific location, in a plurality of methods disclosed herein. In an aspect, a second plurality of sonography images are made in a pre-determined pattern on the skin. In an aspect, a second plurality of sonography images are made in a pre-determined pattern on the skin and the second number of sonographic characteristics is determined at pre-determined positions within the pattern. In an aspect, the second number of sonographic characteristics is determined from a portion or subset of the second plurality of sonography images obtained. In an aspect, the second number of sonographic characteristics at a location is the average number of sonographic characteristics in the plurality of images obtained at that location. In an aspect, the second number of sonographic characteristics at a location is the maximum number of sonographic characteristics in the second plurality of images obtained at that location. In an aspect, the n second umber of sonographic characteristics at a location is the median number of sonographic characteristics in the second plurality of images obtained at that location. In an aspect, the second number of sonographic characteristics at a location is the mode number of sonographic characteristics in the second plurality of images obtained at that location.

In an aspect, a second plurality of sonography images are made at the same locations where a first plurality of sonography images were taken. In one aspect, a second plurality of sonography images are made at some of the same locations where a first plurality of sonography images were taken. In an aspect, a second plurality of sonography images are made near the locations where a first plurality of sonography images were taken. In one aspect, a second plurality of sonography images are made at different locations than where a first plurality of sonography images were taken.

In an aspect, a second threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a second threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a second threshold can be scaled by a factor or a multiple based on the values provided herein. In one aspect, a second threshold can be the same as a first threshold. In an aspect, a second threshold can be greater than a first threshold. In one aspect, a second threshold can be less than a first threshold.

In an aspect, a second number of sonographic characteristics can be 0.1-99.5% of the second threshold, such as 0.1-1%, 0.1-5%, 1-5%, 5-15%, 10-20%, 15-25%, 20-30%, 25-35%, 30-40%, 35-45%, 40-50%, 0.1-25%, 15-35%, 25-50%, 25-75%, 45-55%, 50-60%, 55-65%, 60-70%, 65-75%, 40-55%, 50-75%, 50-99.5%, 70-80%, 75%-85%, 80-90%, 85-95%, 90-99.5%, 65-85%, or 75-99.5% of the second threshold.

In an aspect, M ranges from 2 to 50, such as from 2 to 3, from 2 to 4, from 2 to 5, from 2 to 6, from 2 to 7, from 2 to 8, from 2 to 9, from 2 to 10, from 2 to 15, from 2 to 20, from 2 to 25, from 2 to 30, from 2 to 35, from 2 to 40, or from 2 to 45.

In one aspect, M is determined by the amount by which the second number of sonographic characteristic exceeds the second threshold. In an aspect, the amount by which a threshold established for (M+1) exceeds the second threshold is greater than the amount by which a threshold established for N exceeds the second threshold. In one aspect, the amount by which a threshold established for (M−1) exceeds the second threshold is less than the amount by which a threshold established for M exceeds the second threshold. In an aspect, the value of threshold established for (M+1) is greater than the value of the threshold established for M. In an aspect, the value of threshold established for M is greater than the value of the threshold established for (M−1).

In an aspect, a level M intervention is chosen in accordance with the above "Selection of Intervention Levels" of this disclosure, replacing N with M.

In one aspect, the present disclosure further provides for, and includes, determining whether the second number of sonographic characteristics present is below or equal to a third threshold, continuing to administer the first intervention if the second number of sonographic characteristics present is not less than a third threshold, continuing to take a plurality of sonography images at the first pre-determined frequency if the second number of sonographic characteristics present is not less than the third threshold, administering a third intervention of level-L if the second number of sonographic characteristics present is less than the third threshold and if the first intervention is not of level-0, where L is an integer and L is less than N, and obtaining a plurality of sonography images at a pre-determined frequency corresponding to level-L if the second number of sonographic characteristics present is less than a third threshold.

In an aspect, L ranges from 0 to 50, such as from 0 to 3, from 0 to 4, from 0 to 5, from 0 to 6, from 0 to 7, from 0 to 8, from 0 to 9, from 0 to 10, from 0 to 15, from 0 to 20, from 0 to 25, from 0 to 30, from 0 to 35, from 0 to 40, or from 0 to 45.

In one aspect, L is determined by the amount by which a number of sonographic characteristics is less than the third threshold. In an aspect, the amount by which a threshold established for (L−1) is less than the third threshold is greater than the amount by which a threshold established for L is less than the third threshold. In one aspect, the amount by which a threshold established for (L+1) is less than the third threshold is less than the amount by which a threshold established for L is less than the third threshold. In an aspect, the value of threshold established for (L+1) is greater than the value of the threshold established for L. In an aspect, the value of threshold established for L is greater than the value of the threshold established for (L−1).

In an aspect, a third threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a third threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a third threshold can be scaled by a factor or a multiple based on the values provided herein. In one aspect, a third threshold can be equal to a second threshold. In an aspect, a third threshold can be greater than a second threshold. In one aspect, a third threshold can be less than a second threshold. In one aspect, a third threshold can be the same as a first threshold. In one aspect, a third threshold is equal to a first threshold. In an aspect, a third threshold can be greater than a first threshold. In one aspect, a third threshold can be less than a first threshold.

In an aspect, a second number of sonographic characteristics can be 0.1-99.5% of the third threshold, such as 0.1-1%, 0.1-5%, 1-5%, 5-15%, 10-20%, 15-25%, 20-30%, 25-35%, 30-40%, 35-45%, 40-50%, 0.1-25%, 15-35%, 25-50%, 25-75%, 45-55%, 50-60%, 55-65%, 60-70%, 65-75%, 40-55%, 50-75%, 50-99.5%, 70-80%, 75%-85%, 80-90%, 85-95%, 90-99.5%, 65-85%, or 75-99.5% of the third threshold.

In an aspect, a level L intervention is chosen in accordance with the above "Selection of Intervention Levels" of this disclosure, replacing N with L.

In an aspect, a level-N intervention is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface. In an aspect, a level-M intervention is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface. In an aspect, a level-L intervention is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

Methods of Slowing the Progression of Skin and Tissue Damage

In one aspect, the present disclosure provides for, and includes, a method of slowing the progression of skin and tissue damage in a patient in need thereof, the method comprising the steps of: obtaining a plurality of sonography images in the patient, identifying a sonographic characteristic in the plurality of sonography images, determining a first number of sonographic characteristics present in the plurality of sonography images, continuing to administer the current intervention of level-K if the first number of sonographic characteristics is below or equal to a first threshold, continuing to take a plurality of sonography images at a pre-determined frequency corresponding to level-K if the first number of sonographic characteristics is below or equal to the first threshold, administering a new intervention of level-N if the number of sonographic characteristics exceeds the first threshold, where N has a value greater than K, and taking a plurality of sonography images at a pre-determined frequency corresponding to level-N if the number of sonographic characteristics exceeds the first threshold.

In an aspect, a patient in need thereof is a patient experiencing a change of care, a change in mobility, a change in nutrition, a change in sensory perception, or a combination thereof. In one aspect, a patient in need thereof is a patient having developed an open wound. In an aspect, a patient in need thereof is a patient having recovered from an open wound. In one aspect, a patient in need thereof is a patient receiving surgery. In an aspect, a patient in need thereof is a patient recovering from surgery. In an aspect, a patient in need thereof is a patient receiving spinal analgesics or sacral analgesics during a surgery. In one aspect, a patient in need thereof is a patient receiving a surgery for a duration of four or more hours, such as five or more hours, six or more hours, seven or more hours, eight or more hours, nine or more hours, ten or more hours, eleven or more hours, or twelve or more hours. In an aspect, a surgery has a duration of one or more hours, such as two or more hours, or three or more hours.

In an aspect, a plurality of sonography images is taken at or around one or more body locations selected from the group consisting of sternum, a sacrum, a heel, a scapula (os latum scapularum), an elbow, an ear, and other fleshy tissues over a bony prominence of a patient. In an aspect, a plurality of sonography images is taken at and around one or more anatomical sites in long-term contact with a medical device, an anatomical site is selected from the group consisting of a cheek, a nose, a chest, a stomach, and a lower abdomen area. In an aspect, a plurality of sonography images is separated into sub-groups for analysis based on the general location at which a measurement is taken. In an aspect, the first number of sonographic characteristics is determined from a subset of the plurality of sonography images. In one aspect, a plurality of sonography images is taken at locations located on one or more concentric circles centered around an anatomical site. In an aspect, a plurality of sonography images is taken at locations located on a straight line at approximately equidistance from an anatomical site.

In an aspect, a first number of sonographic characteristics may be determined from a plurality of sonography images made at a certain location, or in close proximity around a specific location, in a plurality of methods. In an aspect, a plurality of sonography images are made in a pre-determined pattern on the skin. In an aspect, a plurality of sonography images are made in a pre-determined pattern on the skin and the first number of sonographic characteristics is determined at pre-determined positions within the pattern. In an aspect, the first number of sonographic characteristics is determined from a portion or subset of the plurality of sonography images obtained. In an aspect, the first number of sonographic characteristics at a location is the average number of sonographic characteristics in the plurality of images obtained at that location. In an aspect, the first number of sonographic characteristics at a location is the maximum number of sonographic characteristics in the plurality of images obtained at that location. In an aspect, the first number of sonographic characteristics at a location is the median number of sonographic characteristics in the plurality of images obtained at that location. In an aspect, the first number of sonographic characteristics at a location is the mode number of sonographic characteristics in the plurality of images obtained at that location.

In an aspect, a first threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a first threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a first threshold can be scaled by a factor or a multiple based on the values provided herein.

In an aspect, K ranges from 2 to 50, such as from 2 to 3, from 2 to 4, from 2 to 5, from 2 to 6, from 2 to 7, from 2 to 8, from 2 to 9, from 2 to 10, from 2 to 15, from 2 to 20, from 2 to 25, from 2 to 30, from 2 to 35, from 2 to 40, or from 2 to 45.

In an aspect, K is determined by the amount by which the number of sonographic characteristics exceeds the threshold. In an aspect, the amount by which a number of sonographic characteristics exceeds a threshold established for (K+1) is greater than the amount by which a number of sonographic characteristics exceeds a threshold established for K. In one aspect, the amount by which a number of sonographic characteristics exceeds a threshold established for (K−1) is less than the amount by which a number of sonographic characteristics exceeds a threshold established for K.

In an aspect, a level K intervention is chosen in accordance with the above "Selection of Intervention Levels" of this disclosure, replacing N with K.

In an aspect, the present disclosure further provides for, and includes, determining whether the first number of sonographic characteristics present is less than a second threshold, administering an intervention of level-L if the first number of sonographic characteristics is less than a second threshold, where L has a non-negative value lesser than K, and obtaining a plurality of sonography images at a predetermined frequency corresponding to level-L if the first number of sonographic characteristics is less than the second threshold.

In an aspect, the second threshold is equal to the first threshold. In an aspect, a second threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a second threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a second threshold can be scaled by a factor or a multiple based on the values provided herein. In one aspect, a second threshold is equal to the first threshold. In an aspect, a second threshold can be greater than a first threshold. In one aspect, a second threshold can be less than a first threshold.

In an aspect, L can be K−1, K−2, K−3, K−4, K−5, K−6, K−7, K−8, K−9, or K−10. In one aspect, L is K−1 if a number of sonographic characteristic is 90-99.5% of the second threshold, such as 90-95%, 91-96%, 92-97%, 93-98%, 94-99%, or 95-99.5% of the second threshold, unless K−1 is less than 0, in which case L would be 0. In an aspect, L is K−2 if a number of sonographic characteristic is 80-89.9% of the second threshold, such as 80-85%, 81-86%, 82-87%, 83-88%, 84-89%, or 85-89.9% of the second threshold, unless K−2 is less than 0, in which case L would be 0. In one aspect, L is K−3 if a number of sonographic characteristic is 70-79.9% of the second threshold, such as 70-75%, 71-76%, 72-77%, 73-78%, 74-79%, or 75-79.9% of the second threshold, unless K−3 is less than 0, in which case L would be 0. In an aspect, L is K−4 if a number of sonographic characteristic is 60-69.9% of the second threshold, such as 60-65%, 61-66%, 62-67%, 63-68%, 64-69%, or 65-69.9% of the second threshold, unless K−4 is less than 0, in which case L would be 0. In one aspect, L is K−5 if a number of sonographic characteristic is 50-59.9% of the second threshold, such as 50-55%, 51-56%, 52-57%, 53-58%, 54-59%, or 55-59.9% of the second threshold, unless K−5 is less than 0, in which case L would be 0. In an aspect, L is K−6 if a number of sonographic characteristic is 40-49.9% of the second threshold, such as 40-45%, 41-46%, 42-47%, 43-48%, 44-49%, or 45-49.9% of the second threshold, unless K−6 is less than 0, in which case L would be 0. In one aspect, L is K−7 if a number of sonographic characteristic is 30-39.9% of the second threshold, such as 30-35%, 31-36%, 32-37%, 33-38%, 34-39%, or 35-39.9% of the second threshold, unless K−7 is less than 0, in which case L would be 0. In an aspect, L is K−8 if a number of sonographic characteristic is 20-29.9% of the second threshold, such as 20-25%, 21-26%, 22-27%, 23-28%, 24-29%, or 25-29.9% of the second threshold, unless K−8 is less than 0, in which case L would be 0. In one aspect, L is K−9 if a number of sonographic characteristic is 10-19.9% of the second threshold, such as 10-15%, 11-16%, 12-17%, 13-18%, 14-19%, or 15-19.9% of the second threshold, unless K−9 is less than 0, in which case L would be 0. In an aspect, L is K−10 if a number of sonographic characteristic is 0.1-9.9% of the second threshold, such as 0.1-5%, 1-6%, 2-7%, 3-8%, 4-9%, or 5-9.9% of the second threshold, unless K−10 is less than 0, in which case L would be 0.

Methods of Identifying and Treating a Patient in Need of Intervention for Pressure Ulcer In an aspect, the present disclosure provides for, and includes, a method of identifying and treating a patient in need of an intervention, the method comprising the steps of: obtaining a plurality of sonography images at an anatomic site of the patient, identifying a sonographic characteristic in the plurality of sonography images, determining a number of sonographic characteristics from the plurality of sonography images, determining whether the number of sonographic characteristics exceeds a threshold corresponding to level-N, where N is greater than or equal to 2, administering the intervention to the anatomic site if the number of sonographic characteristics exceeds the threshold, and taking a plurality of sonography images every two hours if the number of sonographic characteristic exceeds the threshold.

In an aspect, the anatomical site is selected from the group consisting of a sternum, a sacrum, a heel, a scapula (os latum scapularum), an elbow, an ear, and other fleshy tissues over a bony prominence of a patient.

In an aspect, intervention for pressure ulcer is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

In one aspect, the present disclosure provides for, and includes, a method of identifying and treating a patient in need of application of a barrier cream to the patient's heel, the method comprising the steps of: obtaining a plurality of sonography images at the heel of the patient, identifying a sonographic characteristic in the plurality of sonography images, determining a number of sonographic characteristics from the plurality of sonography images, determining whether the number of sonographic characteristics exceeds a threshold corresponding to level-N, where N is greater than or equal to 2, administering the barrier cream to the heel if the number of sonographic characteristics exceeds the threshold, and taking a plurality of sonography images every two hours if the number of sonographic characteristic exceeds the threshold. In an aspect, a plurality of sonographic images are made at least once every hour or at least once every half an hour if the number of sonographic characteristics exceeds the threshold.

In one aspect, the present disclosure provides for, and includes, a method of identifying and treating a patient in need of application of a neuro-muscular stimulation to the patient's heel, the method comprising the steps of: obtaining a plurality of sonography images at the heel of the patient, identifying a sonographic characteristic in the plurality of sonography images, determining a number of sonographic characteristics from the plurality of sonography images, determining whether the number of sonographic characteristics exceeds a threshold corresponding to level-N, where N is greater than or equal to 2, administering the neuro-muscular stimulation to the heel if the number of sonographic characteristics exceeds the threshold, and taking a plurality of sonography images every hour if the number of sonographic characteristic exceeds the threshold. In an aspect, a plurality of sonographic images are made at least once every hour or at least once every half an hour if the number of sonographic characteristics exceeds the threshold.

In an aspect, the present disclosure provides for, and includes, a method of identifying and treating a patient in need of application of a topical cream to the patient's heel, the method comprising the steps of: obtaining a plurality of sonography images at the heel of the patient, identifying a sonographic characteristic in the plurality of sonography images, determining a number of sonographic characteristics from the plurality of sonography images, determining whether the number of sonographic characteristics exceeds a threshold corresponding to level-N, where N is greater than or equal to 2, administering the topical cream to the heel if the number of sonographic characteristics exceeds the threshold, and taking a plurality of sonography images every half an hour if the number of sonographic characteristic exceeds the threshold.

In an aspect, the present disclosure provides for, and includes, a method of identifying and treating a patient in need of application of a heel boot to the patient's heel, the method comprising the steps of: obtaining a plurality of sonography images at the heel of the patient, identifying a sonographic characteristic in the plurality of sonography images, determining a number of sonographic characteristics from the plurality of sonography images, determining whether the number of sonographic characteristics exceeds a threshold corresponding to level-N, where N is greater than or equal to 2, administering the heel boot to the heel if the number of sonographic characteristics exceeds the threshold, and taking a plurality of sonography images every ten hours if the number of sonographic characteristic exceeds the threshold.

In one aspect, the present disclosure provides for, and includes, a method of identifying and treating a patient in need of application of a barrier cream to the patient's sacrum, the method comprising the steps of: obtaining a plurality of sonography images at the sacrum of the patient, identifying a sonographic characteristic in the plurality of sonography images, determining a number of sonographic characteristics from the plurality of sonography images, determining whether the number of sonographic characteristics exceeds a threshold corresponding to level-N, where N is greater than or equal to 2, administering the barrier cream to the sacrum if the number of sonographic characteristics exceeds the threshold, and taking a plurality of sonography images every six hours if the number of sonographic characteristic exceeds the threshold. In an aspect, a plurality of sonography images are made at least once every four hours, at least once every three hours, at least once every two hours, at least once an hour, or at least once every half an hour if the number of sonographic characteristics exceeds the threshold.

In an aspect, the present disclosure provides for, and includes, a method of identifying and treating a patient in need of application of a neuro-muscular stimulation to the patient's sacrum, the method comprising the steps of: obtaining a plurality of sonography images at the sacrum of the patient, identifying a sonographic characteristic in the plurality of sonography images, determining a number of sonographic characteristics from the plurality of sonography images, determining whether the number of sonographic characteristics exceeds a threshold corresponding to level-N, where N is greater than or equal to 2, administering the neuro-muscular stimulation to the sacrum if the number of sonographic characteristics exceeds the threshold, and taking a plurality of sonography images every four hours if the number of sonographic characteristic exceeds the threshold. In an aspect, a plurality of sonography images are made at least once every three hours, at least once every two hours, at least once an hour, or at least once every half an hour if the number of sonographic characteristics exceeds the threshold.

In one aspect, the present disclosure provides for, and includes, a method of identifying and treating a patient in need of application of a topical cream to the patient's sacrum, the method comprising the steps of: obtaining a plurality of sonography images at the sacrum of the patient, identifying a sonographic characteristic in the plurality of sonography images, determining a number of sonographic characteristics from the plurality of sonography images, determining whether the number of sonographic characteristics exceeds a threshold corresponding to level-N, where N is greater than or equal to 2, administering the topical cream to the sacrum if the number of sonographic characteristics exceeds the threshold, and taking a plurality of sonography images every two hours if the number of sonographic characteristic exceeds the threshold. In an aspect, a plurality of sonography images are made at least once an hour or at least once every half an hour if the number of sonographic characteristics exceeds the threshold.

In one aspect, the present disclosure provides for, and includes, a method of identifying and treating a patient in need of application of therapeutic ultrasound, the method comprising the steps of: obtaining a plurality of sonography images at an anatomic site of the patient, identifying a sonographic characteristic in the plurality of sonography images, determining a number of sonographic characteristics from the plurality of sonography images, determining whether the number of sonographic characteristics exceeds a threshold corresponding to level-N, where N is greater than or equal to 2, administering the therapeutic ultrasound to the anatomic site if the number of sonographic characteristics exceeds the threshold, and taking a plurality of sonography images every two hours if the number of sonographic characteristic exceeds the threshold. In an aspect, an anatomical site is selected from the group consisting of a sternum, a sacrum, a heel, a scapula (os latum scapularum), an elbow, an ear, and other fleshy tissues over a bony prominence of a patient.

In one aspect, the present disclosure provides for, and includes, a method of identifying and treating a patient in need of application of shockwave therapy, the method comprising the steps of: obtaining a plurality of sonography images at an anatomic site of the patient, identifying a sonographic characteristic in the plurality of sonography images, determining a number of sonographic characteristics from the plurality of sonography images, determining whether the number of sonographic characteristics exceeds a threshold corresponding to level-N, where N is greater than or equal to 2, administering the shockwave therapy to the anatomic site if the number of sonographic characteristics exceeds the threshold, and taking a plurality of sonography images every two hours if the number of sonographic characteristic exceeds the threshold. In an aspect, an anatomical site is selected from the group consisting of a sternum, a sacrum, a heel, a scapula (os latum scapularum), an elbow, an ear, and other fleshy tissues over a bony prominence of a patient. In one aspect, shockwave therapy is provided via electromagnetic pulse or pressurized air.

In one aspect, the present disclosure provides for, and includes, a method of identifying and treating a patient in need of application of a 30-degree wedge, the method comprising the steps of: obtaining a plurality of sonography images at an anatomic site of the patient, identifying a sonographic characteristic in the plurality of sonography images, determining a number of sonographic characteristics from the plurality of sonography images, determining whether the number of sonographic characteristics exceeds a threshold corresponding to level-N, where N is greater than or equal to 2, administering the 30-degree wedge to the anatomic site if the number of sonographic characteristics exceeds the threshold, and taking a plurality of sonography images every two hours if the number of sonographic characteristic exceeds the threshold. In an aspect, an anatomical site is selected from the group consisting of a sternum, a sacrum, a heel, a scapula (os latum scapularum), an elbow, an ear, and other fleshy tissues over a bony prominence of a patient.

In one aspect, the present disclosure provides for, and includes, a method of identifying and treating a patient in need of application of a composite dressing, the method comprising the steps of: obtaining a plurality of sonography images at an anatomic site of the patient, identifying a sonographic characteristic in the plurality of sonography images, determining a number of sonographic characteristics from the plurality of sonography images, determining whether the number of sonographic characteristics exceeds a threshold corresponding to level-N, where N is greater than or equal to 2, administering the composite dressing to the anatomic site if the number of sonographic characteristics exceeds the threshold, and taking a plurality of sonography images every two hours if the number of sonographic characteristic exceeds the threshold. In an aspect, an anatomical site is selected from the group consisting of a sternum, a sacrum, a heel, a scapula (os latum scapularum), an elbow, an ear, and other fleshy tissues over a bony prominence of a patient.

In one aspect, the present disclosure provides for, and includes, a method of identifying and treating a patient in need of a hybrid mattress, the method comprising the steps of: obtaining a plurality of sonography images at an anatomic site of the patient, identifying a sonographic characteristic in the plurality of sonography images, determining a number of sonographic characteristics from the plurality of sonography images, determining whether the number of sonographic characteristics exceeds a threshold corresponding to level-N, where N is greater than or equal to 2, administering the hybrid mattress to the anatomic site if the number of sonographic characteristics exceeds the threshold, and taking a plurality of sonography images every two hours if the number of sonographic characteristic exceeds the threshold. In an aspect, an anatomical site is selected from the group consisting of a sternum, a sacrum, a heel, a scapula (os latum scapularum), an elbow, an ear, and other fleshy tissues over a bony prominence of a patient.

In one aspect, the present disclosure provides for, and includes, a method of identifying and treating a patient in need of a dynamic mattress, the method comprising the steps of: obtaining a plurality of sonography images at an anatomic site of the patient, identifying a sonographic characteristic in the plurality of sonography images, determining a number of sonographic characteristics from the plurality of sonography images, determining whether the number of sonographic characteristics exceeds a threshold corresponding to level-N, where N is greater than or equal to 2, administering the dynamic mattress to the anatomic site if the number of sonographic characteristics exceeds the threshold, and taking a plurality of sonography images every two hours if the number of sonographic characteristic exceeds the threshold. In an aspect, an anatomical site is selected from the group consisting of a sternum, a sacrum, a heel, a scapula (os latum scapularum), an elbow, an ear, and other fleshy tissues over a bony prominence of a patient.

In an aspect, the present disclosure provides for, and includes, a method of identifying and moving a bedridden patient in need thereof, the method comprising the steps of: providing a mobility sensor comprising an accelerometer and a gyro sensor; monitor frequency and range of mobilization of the patient; providing an alert when the mobility sensor does not sense a movement more than a quarter turn for a specified period of time; and moving the patient upon the alert.

In an aspect, the present disclosure further provides for, and includes, providing anatomy-specific intervention to an anatomical location of a patient identified as being damaged by a combination of a visual assessment and sonography images. In one aspect, an anatomy-specific intervention is provided to a common site for wound development selected from the group consisting of: toes, heels, a sacrum, a spine, elbows, shoulder blades, occiput, and ischial tuberosity. In an aspect, an anatomy-specific intervention is concurrently provided to a second common site for wound development selected from the group consisting of: toes, heels, a sacrum, a spine, elbows, shoulder blades, occiput, and ischial tuberosity. In one aspect, a first site receiving an anatomy-specific intervention is known to cause a development of a wound at a second site.

Comparison of Bisymmetric Sonography Images to Identify Damaged Tissue

In one aspect, the present disclosure provides for, and includes, a method for identifying damaged tissue, the method comprising the steps of: obtaining a first sonography image from a first location on a patient's skin, obtaining a second sonography image from a second location that is bisymmetric relative to the first location, identifying sonographic characteristics in each of the first and second sonography images, determining the number of sonographic characteristics from each of the first and second sonography image, determining a difference in the number of sonographic characteristics between a first sonography image and a second sonography image, and determining that there is tissue damage at the first or second location if the difference in the number of sonographic characteristics between the first sonography image and the second sonography image exceeds a threshold value.

Figure 4A:
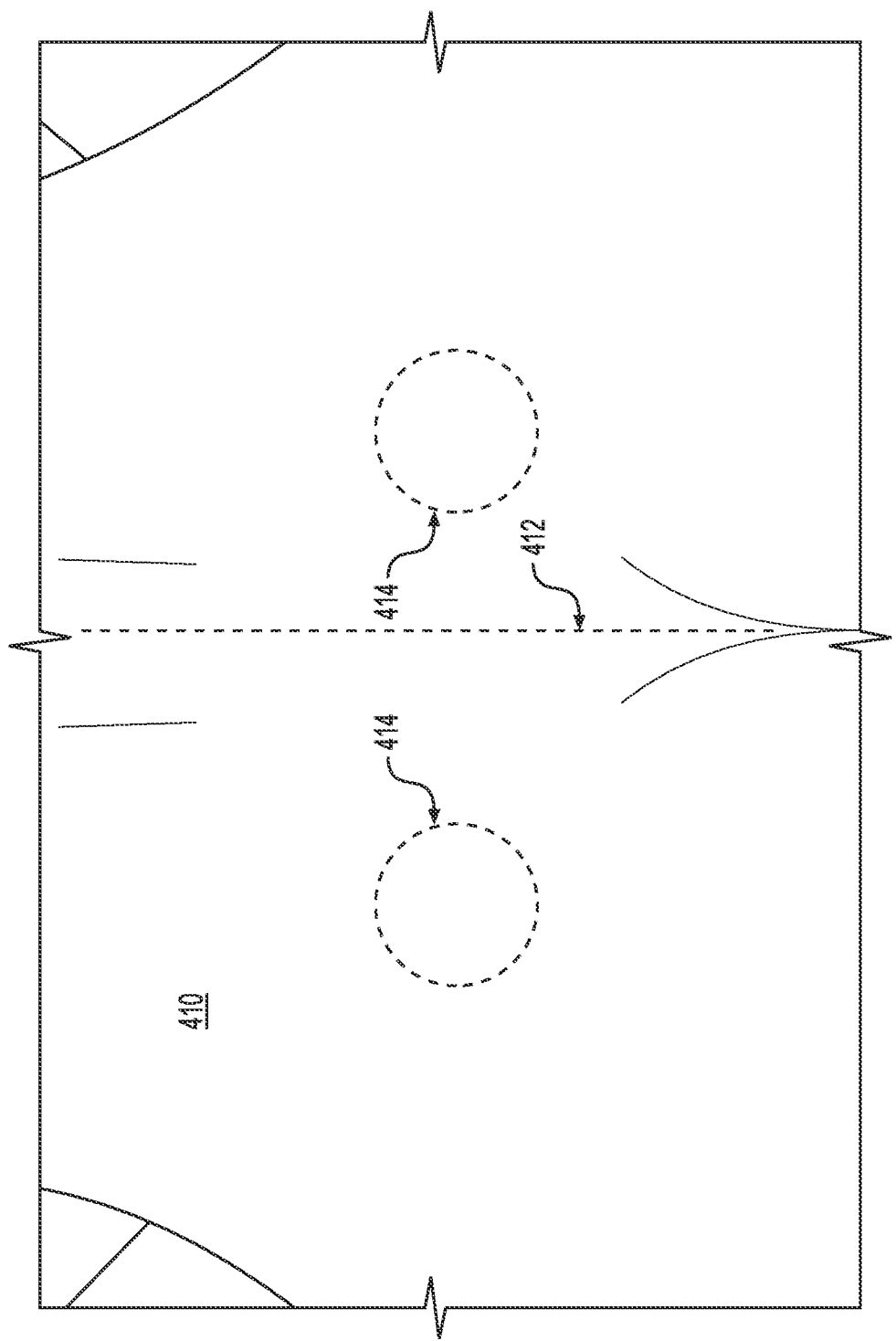
FIG. 4A provides an example of a pair of bisymmetric locations on a sacral region according to the present disclosure.

FIG. 4A depicts the sacral region of the back of a patient 410. A line of symmetry 412 can be drawn down the center of the back, dividing the back into left and right mirror images. Locations 414 are approximately the same distance from line of symmetry 412 and approximately at the same height and are, therefore, considered to be bisymmetric locations on the back of patient 410.

Figure 4B:
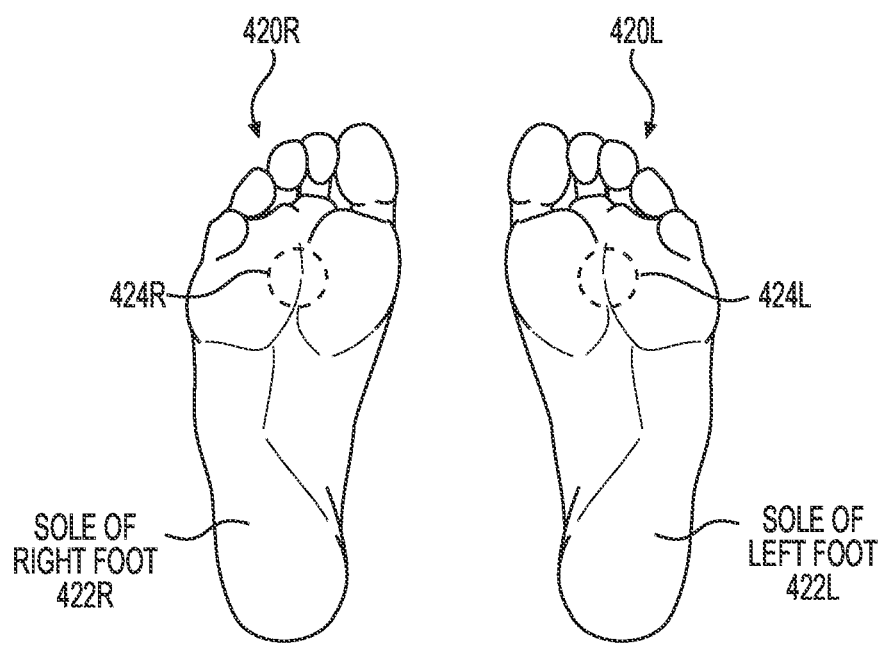
FIG. 4B provides an example of a pair of bisymmetric locations on the bottom side of both feet according to the present disclosure.

FIG. 4B depicts left foot 420L and right foot 420R of a patient 410, as seen if patient 410 were lying on the back on a bed (not shown) and an observer were standing at the foot of the bed. With respect to soles 422L and 422R of feet 420L and 420R, locations 424L and 424R are located at approximately equivalent locations, e.g. the same distance from the posterior surface, i.e. the heel, and the same distance from the medial side of respective foot 420L or 420R and are considered to be bisymmetric locations.

Figure 4C:
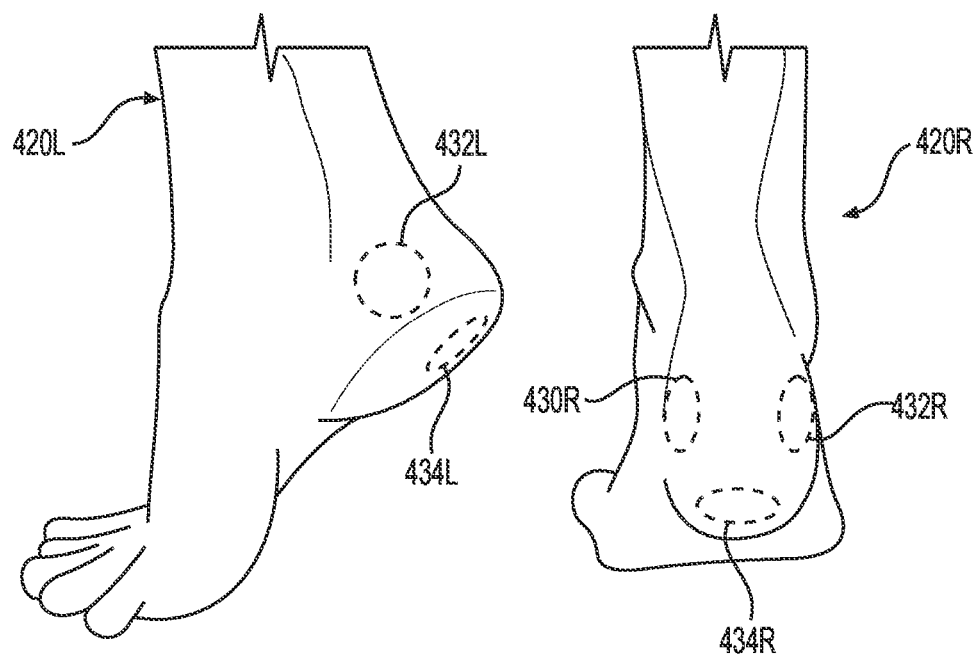
FIG. 4C provides an example of a pair of bisymmetric locations on the lateral sides and soles of both feet according to the present disclosure.

FIG. 4C depicts additional exemplary bisymmetric locations 432L and 432R located on the lateral sides of feet 420L and 420R, and bisymmetric locations 434L and 434R located on respective soles 422L and 422R of feet 420L and 420R. In an aspect, locations 432R and 430R are considered bisymmetric with respect to foot 420R when considered alone without reference to foot 420L.

Without being limited to a particular theory, comparison of sonography images taken at bisymmetric locations can compensate for an offset of readings of a particular patient from a population of patients. For example, a patient may be dehydrated on a particular day when measurements are being made. A comparison of the number of sonographic characteristics of healthy tissue from the same patient, while in a dehydrated condition, may be shifted from the number of sonographic characteristics of the same tissue at the same location when the patient is fully hydrated. If the tissue at one location is healthy while the tissue at the bisymmetric location is damaged, a comparison of the readings taken at the bisymmetric locations will exclude the "common mode" effect of dehydration variation at both locations and provide a more robust indication that tissue is damaged at one location.

Figure 6:
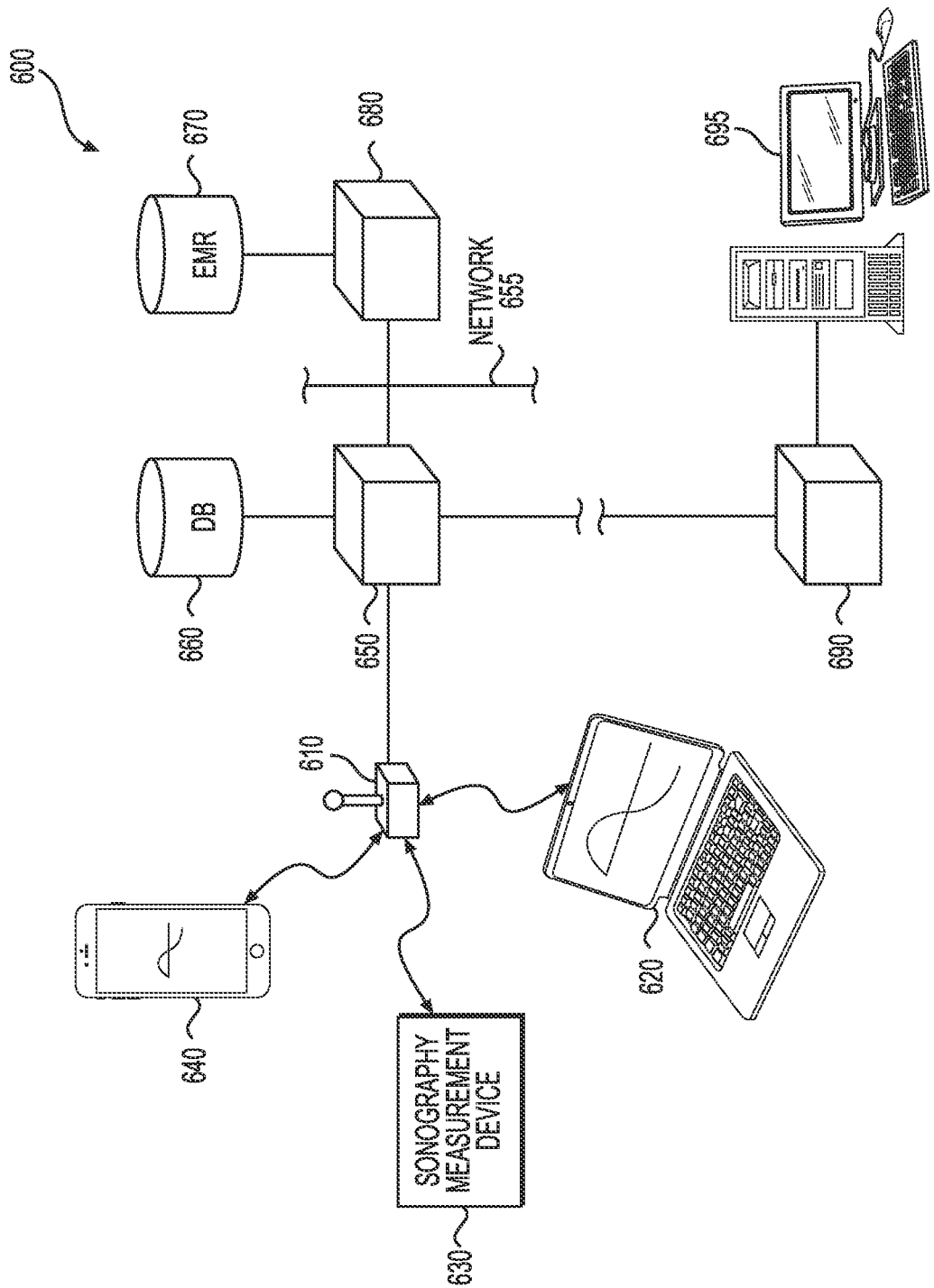
FIG. 6 depicts an integrated system for measurement, evaluation, storage, and transfer of sonography images, according to the present disclosure.
Figure 7A:
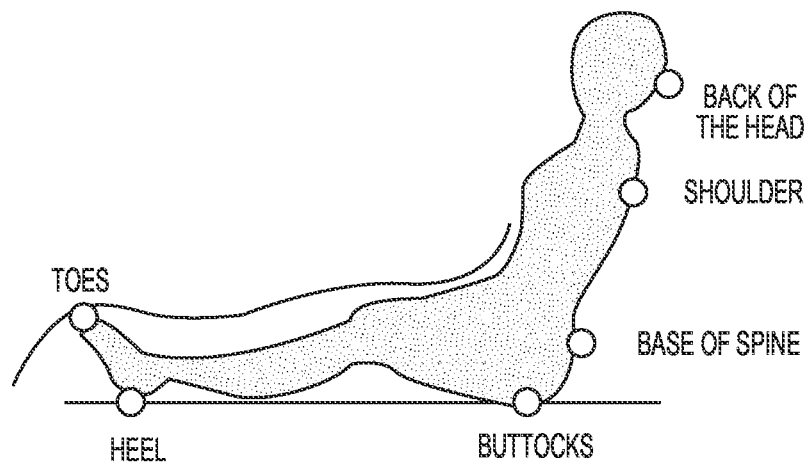
FIGS. 7A, 7B, 7C, and 7D illustrate various pressure points on a patient's body at different positions.
Figure 7B:
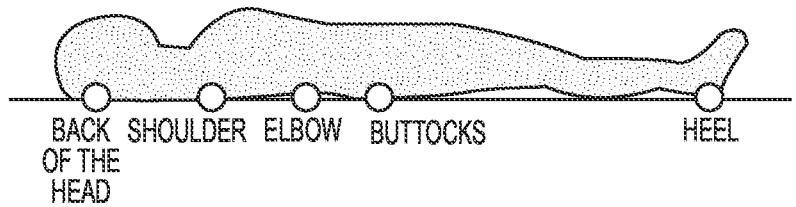
Figure 7C:
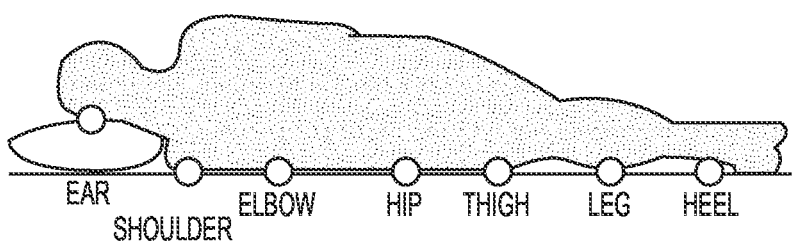
Figure 7D:
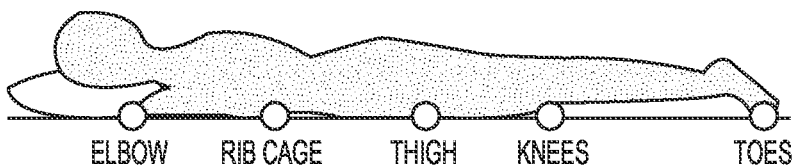

A sonography image apparatus 600 as provided in FIG. 6 may be used to take measurements at multiple locations, for example a first measurement at a first location and a second measurement at a second location that is bisymmetric relative to the first location. In an aspect, apparatus 600 comprises a processor that can be configured by instructions stored on a non-transitory computer-readable medium to determine a characteristic of the measurements taken at multiple locations or parameters associated with or derived from the measurements, for example one or more of a difference between, the number of sonographic characteristics determined from multiple measurements. In one aspect, apparatus 600 comprises a display configured to show one or more parameters associated with the measurements, for example a difference between the number of sonographic characteristics determined from sonography images taken at two bisymmetric locations.

In one aspect, a number of sonographic characteristics is determined, where a number that exceeds a predetermined threshold is indicative of tissue damage at one of the locations where the corresponding sonography images were taken. In an aspect, the number of sonographic characteristics obtained at each bisymmetric locations are determined and compared. In one aspect, medians or modes of number of sonographic characteristics obtained at each bisymmetric locations are determined and compared. In an aspect, the damage is indicated to be at the location associated with the larger number of sonographic characteristics. In one aspect, the damage is indicated to be at the location associated with the smaller number of sonographic characteristics. In an aspect, determination of whether there is tissue damage comprises one or more of comparison of individual numbers of sonographic characteristics with one or more predetermined ranges or thresholds and comparison of the difference with one or more predetermined ranges or thresholds. In an aspect, a predetermined range may be from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a predetermined range may be from 0.1 to 4.0, such as from 0.5 to 4.0, from 0.1 to 3.5, from 1.0 to 3.5, from 1.5 to 4.0, from 1.5 to 3.5, from 2.0 to 4.0, from 2.5 to 3.5, from 2.0 to 3.0, from 2.0 to 2.5, or from 2.5 to 3.0. In one aspect, a predetermined range may be from 4.1 to 8.0, such as from 4.5 to 8.0, from 4.1 to 7.5, from 5.0 to 7.5, from 5.5 to 7.0, from 5.5 to 7.5, from 6.0 to 8.0, from 6.5 to 7.5, from 6.0 to 7.0, from 6.0 to 6.5, or from 6.5 to 7.0. In one aspect, a predetermined threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a predetermined threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a predetermined range or threshold can be scaled by a factor or a multiple based on the values provided herein. It will be understood that a predetermined value is not limited by design, but rather, one of ordinary skill in the art would be capable of choosing a predetermined value. In one aspect, ranges and thresholds of the present disclosure are varied according to the specific bisymmetric locations, the portion of a patient's body on which measurements are being made, or one or more characteristics of the patient such as age, height, weight, family history, ethnic group, and other physical characteristics or medical conditions.

One or more regions may be defined on a body. In an aspect, measurements made within a region are considered comparable to each other. A region may be defined as an area on the skin of the body wherein measurements may be taken at any point within the area. In an aspect, a region corresponds to an anatomical region (e.g., heel, ankle, lower back). In an aspect, a region may be defined as a set of two or more specific points relative to anatomical features wherein measurements are taken only at the specific points. In an aspect, a region may comprise a plurality of non-contiguous areas on the body. In an aspect, the set of specific locations may include points in multiple non-contiguous areas.

In an aspect, a region is defined by surface area. In an aspect, a region may be, for example, between 5 and 200 $cm^2$, between 5 and 100 $cm^2$, between 5 and 50 $cm^2$, or between 10 and 50 $cm^2$, between 10 and 25 $cm^2$, or between 5 and 25 $cm^2$.

In an aspect, measurements may be made in a specific pattern or portion thereof. In an aspect, the pattern of readings is made in a pattern with the target area of concern in the center. In an aspect, measurements are made in one or more circular patterns of increasing or decreasing size, T-shaped patterns, a set of specific locations, or randomly across a tissue or region. In an aspect, a pattern may be located on the body by defining a first measurement location of the pattern with respect to an anatomical feature with the remaining measurement locations of the pattern defined as offsets from the first measurement position.

In one aspect, the sonography measurement device of the present disclosure may further comprise a plurality of contact sensors on the same planar surface as, and surrounding, each of the receivers to ensure complete contact of the device to the skin surface. The plurality of contact sensors may be a plurality of pressure sensors, a plurality of light sensors, a plurality of temperature sensors, a plurality of pH sensors, a plurality of perspiration sensors, a plurality of ultrasonic sensors, a plurality of bone growth stimulator sensors, or a plurality of a combination of these sensors. In an aspect, the plurality of contact sensors may comprise four, five, six, seven, eight, nine, or ten or more contact sensors.

Figure 5A:
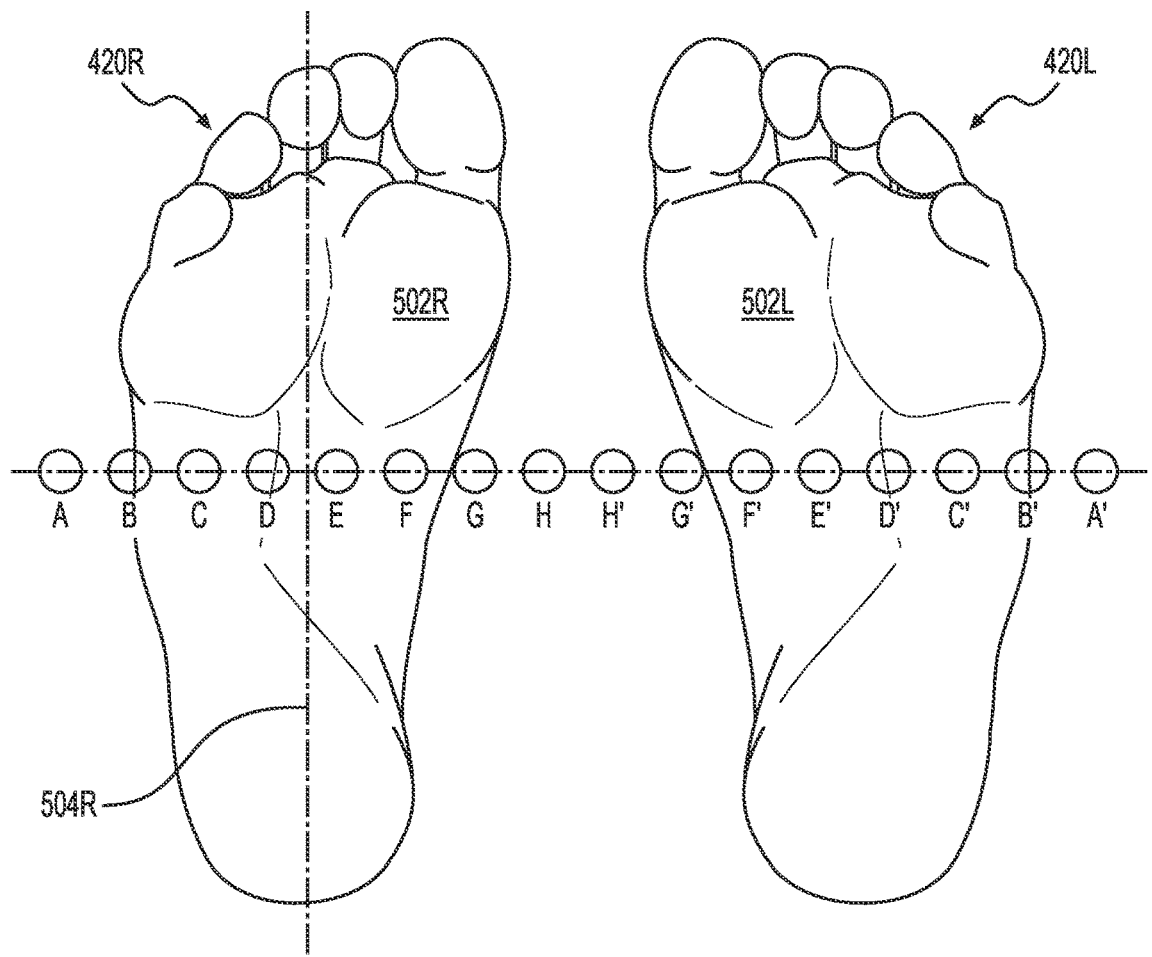
FIG. 5A illustrates locations on the left and right feet for sonography imaging according to the present disclosure.
Figure 5B:
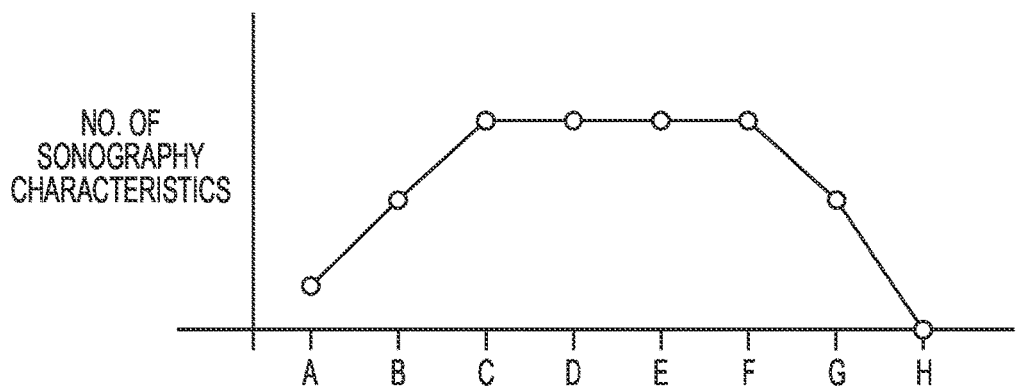
FIG. 5B is a plot of the number of sonographic characteristics associated with known relative locations for identifying bisymmetric locations according to the present disclosure.

FIGS. 5A and 5B depict an example of how comparison of number of sonographic characteristics associated with measurements at known relative locations can identify bisymmetric locations, according to the present disclosure. In this example, a sonography measurement device 630 is presented at non-overlapping locations, marked "A" to "H" in FIG. 5A, across a contact area 502R of a right foot, e.g., 420R of FIG. 4C. The number of sonographic characteristics measured at each location are plotted in the graph of FIG. 5B. In this example, the number of sonographic characteristics at locations "A" and "H" are low or zero, reflecting the non-overlap of the sonography measurement device 630 with contact area 502R in those locations. The number of sonographic characteristics associated with locations "B" and "G" are higher, as the sonography measurement device 630 overlaps a portion of contact area 502R in those positions. The number of sonographic characteristics for locations C-D-E-F are higher and, in this example, approximately the same, indicating that the sonography measurement device 630 is completely within contact area 502R at those locations. In one aspect, a sonography measurement apparatus such as sonography measurement device 630 may determine that certain locations, for example locations "C" and "F," are bisymmetric with respect to a centerline 504R of right foot 420R. In an aspect, where a similar set of measurements is made at locations A'-H' on left foot 420L, a location on each foot 420L and 420R, for example locations E and E', may be determined to be approximately bisymmetric.

FIG. 6 depicts a schematic depiction of an integrated system 600 for measurement, evaluation, storage, and transfer of sonography images, according to the present disclosure. In this example, system 600 comprises a sonography measurement device 630 that comprises the capability to wirelessly communicate with a WiFi access point 610. Sonography measurement device 630 communicates with one or more of a sonography imaging application running on a server 650, an application running on a laptop computer 620, a smart phone 640, or other digital device. In one aspect, laptop computer 620 and smart phone 640 are carried by a user of sonography measurement device 630, for example a nurse, and an application provides feedback and information to the user. In an aspect, information received from sonography measurement device 630 for a patient is stored in a database 660. In one aspect, information received from sonography measurement device 630 is transferred over a network 655 to another server 680 that stores a portion of information in an electronic medical record (EMR) 670 of a patient. In one aspect, information from sonography measurement device 630 or retrieved from database 660 or EMR 670 is transferred to an external server 690 and then to a computer 695, for example a computer at the office of a doctor who is providing care for a patient.

Methods of Detecting Tissue Damage Before it is Visible

In an aspect, the present disclosure provides for, and includes, a method of detecting tissue damage before it is visible on a patient's skin, the method comprising the steps of: obtaining a plurality of sonography images at a single location at incremental times, identifying sonographic characteristics in each of the plurality of sonography images, determining the number of sonographic characteristics from each of the plurality of sonography images, calculating a slope between the latest number of sonographic characteristics and the immediately prior number of sonographic characteristics, comparing the slope to a threshold value, and determining that there is tissue damage if the slope exceeds the threshold value.

In an aspect, the slope between the latest number of sonographic characteristics and the immediately prior number of sonographic characteristics is indicative of tissue damage. In an aspect, a positive slope between the latest number of sonographic characteristics and the immediately prior number of sonographic characteristics is indicative of worsening tissue damage. In an aspect, a positive slope between the latest number of sonographic characteristics and the immediately prior number of sonographic characteristics is indicative of a pressure ulcer forming.

In an aspect, the present disclosure provides for, and includes, a method of detecting tissue damage before it is visible on a patient's skin, the method comprising the steps of: obtaining a plurality of sonography images at a single location at incremental times, identifying sonographic characteristics in each of the plurality of sonography images, determining the number of sonographic characteristics from each of the plurality of sonography images, calculating a difference value of the maximum number of sonographic characteristics and the minimum number of sonographic characteristics for each incremental time, calculating a derivative of the difference value with respect to time, comparing the derivative to a threshold value, and determining that there is tissue damage if the derivative exceeds the threshold value.

In an aspect, a difference value of the maximum number of sonographic characteristics and the minimum number of sonographic characteristics for each time is indicative of tissue damage. In an aspect, the derivative of difference value with respect to time is calculated from two different times. In an aspect, the derivative of difference value with respect to time is calculated from the two most recent difference values. In an aspect, the derivative of difference value with respect to time is calculated from the difference value measured at two consecutive timepoints. In an aspect, the derivative of difference value with respect to time is calculated from the difference value measured at two non-consecutive timepoints. In an aspect, a derivative that is positive is indicative of worsening tissue damage. In an aspect, a derivative that is positive is indicative of a pressure ulcer forming.

In an aspect, the present disclosure provides for, and includes, a method of detecting tissue damage before it is visible on a patient's skin, the method comprising the steps of: obtaining a plurality of sonography images at a single location at incremental times, identifying sonographic characteristics in each of the plurality of sonography images, determining the number of sonographic characteristics from each of the plurality of sonography images, calculating a difference value of the maximum number of sonographic characteristics and the minimum number of sonographic characteristics for each incremental time, fitting a curve to a predetermined number of the most-recent difference values, calculating a curvature of the fitted curve, comparing the curvature to a threshold value, and determining that there is tissue damage if the curvature exceeds the threshold value.

In an aspect, the curvature of a fitted curve of difference value over time is indicative of tissue damage. In an aspect, an increased curvature of a fitted curve of difference value over time is indicative of worsening tissue damage. In an aspect, an increased curvature of a fitted curve of difference value over time is indicative of a pressure ulcer forming.

In some aspects, a plurality of sonography images are taken at incremental times. In an aspect, incremental times is about once every second, about once every 15 seconds, about once every 30 seconds, about once every minute, about once every 10 minutes, about once every 15 minutes, about once every 30 minutes, about once every hour, about once every 2 hours, about once every 3 hours, about once every 4 hours, about once every 6 hours, about once every 12 hours, about once every 24 hours, about once every day, about once every 2 days, about once every 3 days, about once every 4 days, about once every 5 days, about once every 6 days, about once every 7 days, about once every 8 days, about once every 9 days, about once every 10 days.

In an aspect, a threshold may be about 0.3, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, or 7.5. In one aspect, a threshold may range from 0.1 to 8.0, such as from 0.1 to 1.0, from 1.1 to 2.0, from 2.1 to 3.0, from 3.1 to 4.0, from 4.1 to 5.0, from 5.1 to 6.0, from 6.1 to 7.0, from 7.1 to 8.0, from 0.1 to 7.5, from 0.5 to 8.0, from 1.0 to 7.0, from 1.5 to 6.5, from 2.0 to 6.0, from 3.0 to 5.5, from 3.5 to 5.0, or from 4.0 to 4.5. In an aspect, a threshold can be scaled by a factor or a multiple based on the values provided herein. It will be understood that a threshold is not limited by design, but rather, one of ordinary skill in the art would be capable of choosing a predetermined value. In one aspect, thresholds of the present disclosure are varied according to the specific portion of a patient's body on which measurements are being made, or one or more characteristics of the patient such as age, height, weight, family history, ethnic group, and other physical characteristics or medical conditions.

In an aspect, a number of sonographic characteristics above a predefined threshold value is an indication of sub-epidermal damage that may lead to a pressure ulcer. The time interval between the time when the number of sonographic characteristics first equals or exceeds this threshold and the development of visible symptoms of a pressure ulcer may be a first duration when the number of sonographic characteristics increases linearly. A first duration may be 5 or more days, such as 6 or more days, 7 or more days, 8 or more days, 9 or more days, or 10 or more days.

In another aspect, when the plot of the number of sonographic characteristics over time shows an upward curvature or other deviation above a linear progression, the visible symptoms may be present within a shorter amount of time, for example 2-3 days, 1-4 days, 1-3 days, 1-2 days, or 2-4 days. These numbers of sonographic characteristics values are tracked and the trend of the number of sonographic characteristic values, i.e. the slope and curvature of a curve connecting these number of sonographic characteristic values, is analyzed. In an aspect, the amount by which an incremental number of sonographic characteristics is above a linear prediction based on prior numbers of sonographic characteristics is compared to a predetermined threshold. In an aspect, the amount by which an incremental number of sonographic characteristics is above the most recent prior number of sonographic characteristics is compared to a predetermined threshold. In an aspect, a curvature of the best-fit curve fitted to a predefined number of the most-recent number of sonographic characteristics is compared to a predetermined threshold. In an aspect, the number of sequential numbers of sonographic characteristic that exceeds a predetermined value threshold is compared to a number-of-readings threshold. In each of these aspects, the sonography imaging scanner provides a notification when the comparison parameter exceeds the respective threshold.

In an aspect, the trend analysis may ignore a single number of sonographic characteristic value that is below a threshold if both the prior and subsequent number of sonographic characteristics are above the threshold.

In an aspect, the trend curve of the number of sonographic characteristics is a point-to-point linear connection. In an aspect, the trend curve is a best-fit curve fitted to the number of sonographic characteristics. In an aspect, the fitted curve is required to intersection the most-recent number of sonographic characteristics.

Having now generally described the invention, the same will be more readily understood through reference to the following examples that are provided by way of illustration, and are not intended to be limiting of the present disclosure, unless specified.

EXAMPLES

Example 1: Intervention Levels for Treating Pressure Ulcers in the Heel

Subjects identified as being at risk for pressure ulcers in the heel are treated in accordance with the following scheme:

One or more sonography images of the patient at the heel are obtained. The number of sonographic characteristics is determined. As shown in Table 1, the patient is assigned an intervention level based on the number of sonographic characteristics compared to a threshold. Appropriate interventions corresponding to the assigned intervention levels are performed. Subsequent sonography imaging is also performed at a frequency determined by the assigned intervention level. The assigned intervention level of the patient may be changed (increased or decreased) or kept the same depending on the number of sonographic characteristics of the subsequent measurements.

TABLE 1

EXAMPLE INTERVENTION SCHEME FOR TREATING
A PRESSURE ULCER IN THE HEEL

| Intervention Level | Intervention | Frequency of Subsequent Sonography Imaging Monitoring | Corresponding Sonographic characteristics (SC) Ranges |
|---|---|---|---|
| 0 | provide good nutrition, standard mattress, and/or turn every 24 hours | every 24 hours | SC ≤ threshold |
| 1 | provide a heel boot | every 10 hours | threshold < SC ≤ 105% threshold |
| 2 | change of support surface | at the beginning of each nursing shift | 105% threshold < SC ≤ 110% threshold |
| 3 | apply dressing to back or sides of heel | every 12 hours | 110% threshold < SC ≤ 115% threshold |
| 4 | change to low-friction sheet cover | every 8 hours | 115% threshold < SC ≤ 120% threshold |
| 5 | provide a low-friction padded mattress surface for lower leg | every 6 hours | 120% threshold < SC ≤ 125% threshold |
| 6 | turn patient at a shorter interval | every 4 hours | 125% threshold < SC ≤ 130% threshold |
| 7 | apply barrier cream | every 2 hours | 130% threshold < SC ≤ 135% threshold |
| 8 | apply neuro-muscular stimulation | every 1 hour | 135% threshold < SC ≤ 145% threshold |
| 9 | apply topical cream to enhance perfusion | every 30 minutes | 145% threshold < SC ≤ 150% threshold |
| 10 | provide silicone pad for lower leg | every 15 minutes | 150% threshold < SC |

Example 2: Intervention Levels for Treating Pressure Ulcers in the Sacrum

Subjects identified as being at risk for pressure ulcers in the sacrum are treated in accordance with the following scheme:

One or more sonography images of the patient at the sacrum are obtained. The number of sonographic characteristics is determined. As shown in Table 2, the patient is assigned an intervention level based on the number of sonographic characteristics compared to a threshold number. Appropriate interventions corresponding to the assigned intervention levels are performed at the sacrum. Subsequent sonography imaging is also performed at a frequency determined by the assigned intervention level. The assigned intervention level of the patient may be changed (increased or decreased) or kept the same depending on the number of sonographic characteristics of the subsequent measurements.

TABLE 2

EXAMPLE INTERVENTION SCHEME FOR TREATING
A PRESSURE ULCER IN THE SACRUM

| Intervention Level | Intervention | Frequency of Subsequent Sonography Monitoring | Corresponding Sonographic characteristics (SC) Ranges |
|---|---|---|---|
| 0 | provide good nutrition, standard mattress, and/or turn every 24 hours | every 24 hours | SC ≤ threshold |
| 1 | reposition patient with wedge and/or keep sacrum dry | every 10 hours | threshold < SC ≤ 110% threshold |
| 2 | change mattress to pressure-alleviating mattresses | at the beginning of each nursing shift | 110% threshold < SC ≤ 120% threshold |
| 3 | apply dressing over sacrum | every 12 hours | 120% threshold < SC ≤ 130% threshold |
| 4 | change to dynamic mattress | every 8 hours | 130% threshold < SC ≤ 140% threshold |
| 5 | apply barrier cream | every 6 hours | 140% threshold < SC ≤ 150% threshold |
| 6 | apply neuro-muscular stimulation | every 4 hours | 150% threshold < SC ≤ 160% threshold |
| 7 | apply topical cream to enhance perfusion | every 2 hours | 160% threshold < SC ≤ 170% threshold |

TABLE 2-continued

EXAMPLE INTERVENTION SCHEME FOR TREATING
A PRESSURE ULCER IN THE SACRUM

| Intervention Level | Intervention | Frequency of Subsequent Sonography Monitoring | Corresponding Sonographic characteristics (SC) Ranges |
|---|---|---|---|
| 8 | provide silicone pad under the patient's body | every 1 hour | 170% threshold < SC ≤ 180% threshold |

Example 3: Treatment Decision Pathway for Stratifying Patients and Providing Appropriate Treatments Pressure ulcers are categorized as Stage 1 through Stage 4, with Stage 1 being the least severe. The National Pressure Ulcer Advisory Panel (NPUAP) has defined a Stage 1 ulcer as having intact skin with a localized area of non-blanchable erythema. The erythema (superficial reddening of skin) is "blanchable" if it turns white when pressed and "non-blanchable" if it remains red when pressed, likely due to the presence of red blood cells outside of blood vessels (extravasation). In some patients, blanchable erythema or changes in sensation, temperature, or firmness may precede visual changes. While all patients are potentially at risk, pressure ulcers are more likely to occur in patients who are seriously ill or those who have a neurological condition, impaired mobility, impaired nutrition, poor posture, or a deformity.

Visual skin assessment (VSA) is the current method of identifying a pressure ulcer. A trained healthcare professional assesses the appearance of the skin, visually and tactilely, looking for redness or variations in tissue firmness, tissue temperature, or moisture.

FIG. 1A outlines a currently recommended treatment decision pathway for preventing pressure ulcers in hospital patients, as presented by The National Institute for Health and Care Excellence (NICE) in their clinical guideline *Pressure ulcers: prevention and management*, published 23 Apr. 2014. The guidelines recommend that a risk analysis be performed for every patient admitted to a care facility that exhibits one or more risk factors such as significantly limited mobility, a significant loss of sensation, a previous or current pressure ulcer, a nutritional deficiency, an inability to reposition themselves, or a significant cognitive impairment. Risk assessment is commonly done using a scored checklist, such as the Braden Scale, that assesses the severity of specific risk factors. See, e.g., Bergstrom et al., Nurs Res, 36(4): 205-210 (1987). The scale is composed of six subscales that reflect sensory perception, skin moisture, activity, mobility, friction and shear, and nutritional status.

Through the risk assessment, the patient is identified as (i) having a low risk of developing a pressure ulcer, (ii) being at risk of developing a pressure ulcer, or (iii) being at high risk of developing a pressure ulcer. Depending on the level of risk the patient is classified as having, the patient undergoes different sequences of treatment and follow-up evaluation by visual assessment.

If a patient is identified as having a low risk of developing a pressure ulcer, the patient is simply monitored for a change in clinical status, for example, events such as undergoing surgery, worsening of an underlying condition, or a change in mobility. A patient who uses a wheelchair or sits for prolonged periods may be provided with a high-specification foam chair cushion or equivalent pressure-distributing cushion. If there is no change in clinical status, a low-risk patient will not be reassessed under this set of guidelines and stays within the same treatment and evaluation pathway until he or she is discharged from the care facility.

If a patient is identified as being at risk of developing a pressure ulcer, the patient will be scheduled to be turned, or "rounded," every 6 hours. As with the low-risk patient, a high-spec foam chair cushion may be provided if the patient uses a wheelchair or sits for prolonged periods of time. No other monitoring or intervention is recommended by the NICE guidelines.

If a patient is identified as having a high-risk of developing a pressure ulcer, the patient will receive a high-spec foam mattress as a preventative measure, or is provided with a high-spec chair cushion if they are in a wheelchair or sit for prolonged periods of time. The patient will also be repositioned every 4 hours. The patient will receive a daily VSA for all areas of the body. If an area is found to have non-blanchable erythema, an appropriate intervention will be implemented and that area re-checked by VSA every 2 hours. Areas that do not exhibit non-blanchable erythema are re-checked daily by VSA. A personalized care plan will be developed for each high-risk patient.

This flow chart (FIG. 1A) shows that caregivers spend the majority of their time on high-risk patients. While this may be appropriate, it leaves the at-risk patients unmonitored and they may develop a Stage 1 ulcer before the condition is detected by a caregiver. Furthermore, relying on VSA to detect a problem necessarily means that patients will develop a Stage 1 ulcer before an intervention is selected or implemented. By the time that the damage has progressed to Stage 1, it is likely that the skin will break and become a Stage 2 ulcer despite intervention. There is a clear need to identify tissue damage earlier so that interventions can prevent progression of the subepidermal damage to Stage 1 and beyond.

Figure 1B:
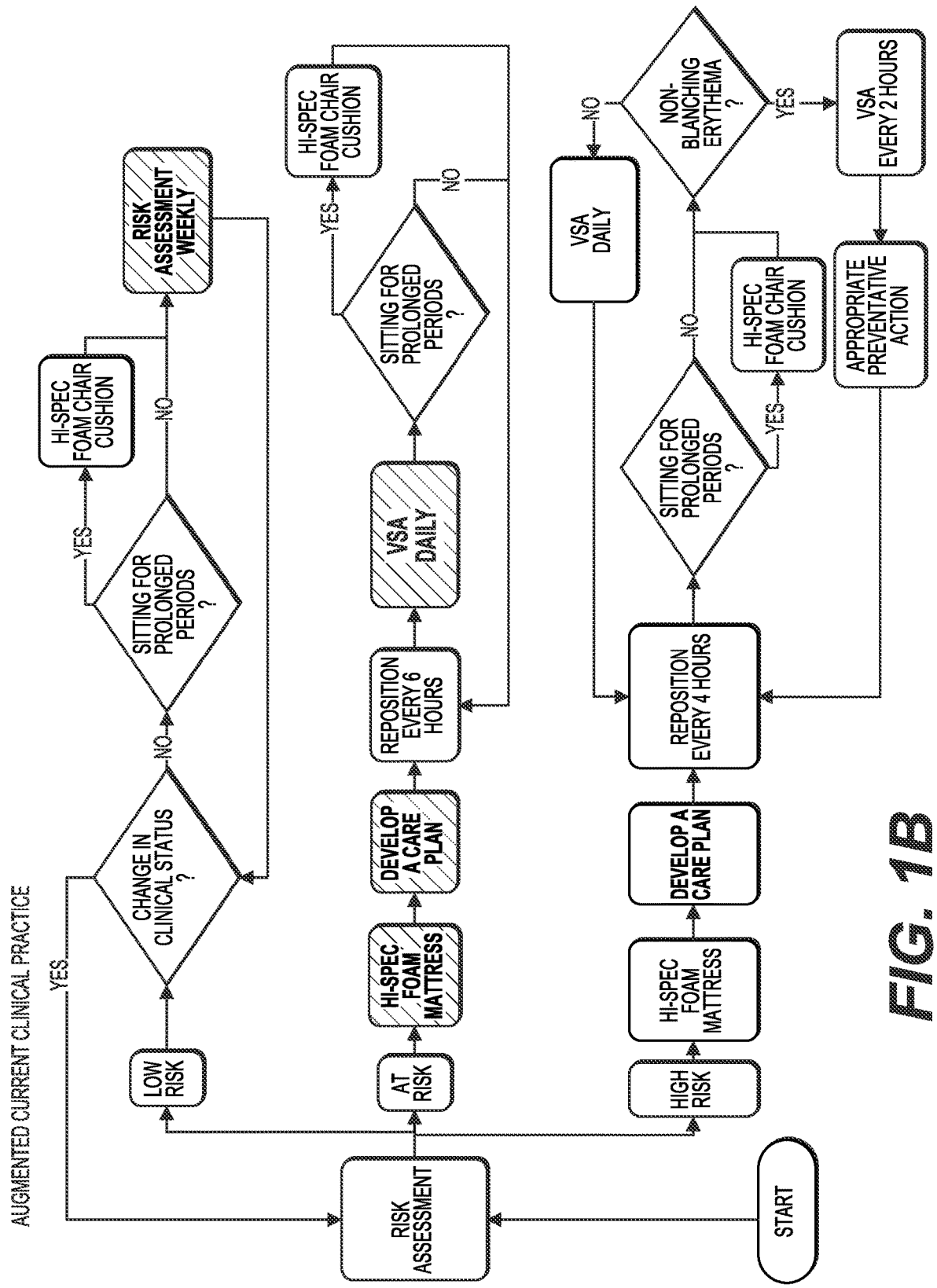
FIG. 1B is an example of a current augmented treatment decision pathway for preventing pressure ulcers as currently implemented at some health care facilities.

FIG. 1B is an example of an augmented treatment decision pathway for preventing pressure ulcers as currently implemented at some health care facilities. The augmented pathway adds monitoring steps to both the at-risk and the low-risk paths. A low-risk patient received a weekly risk assessment, for example completion of the Braden Scale assessment. An at-risk patient will receive a high-spec foam mattress as a preventative measure and will be evaluated daily by VSA. A care plan will be developed for monitoring and treating the at-risk patient. No change is made in the care of a high-risk patient.

The augmented plan has the benefit of providing basic monitoring of all patients for pressure ulcers. However, the additional steps will require additional time, either by requiring more staff or further burdening the existing staff. While superior to the recommended care pathway of FIG. 1A, the care pathway of FIG. 1B requires more resources and still suffers from the limitation that a patient must develop a Stage 1 ulcer before VSA identifies the damage.

Different hospitals and care facilities use different numbers of risk categories. They range from two categories (low-risk and at-risk) to four or more categories, with the addition of categories such as "very-high-risk" to those shown in example of FIG. 1B. Patients are assigned to the various categories based on the results of the initial risk assessment.

Figure 2:
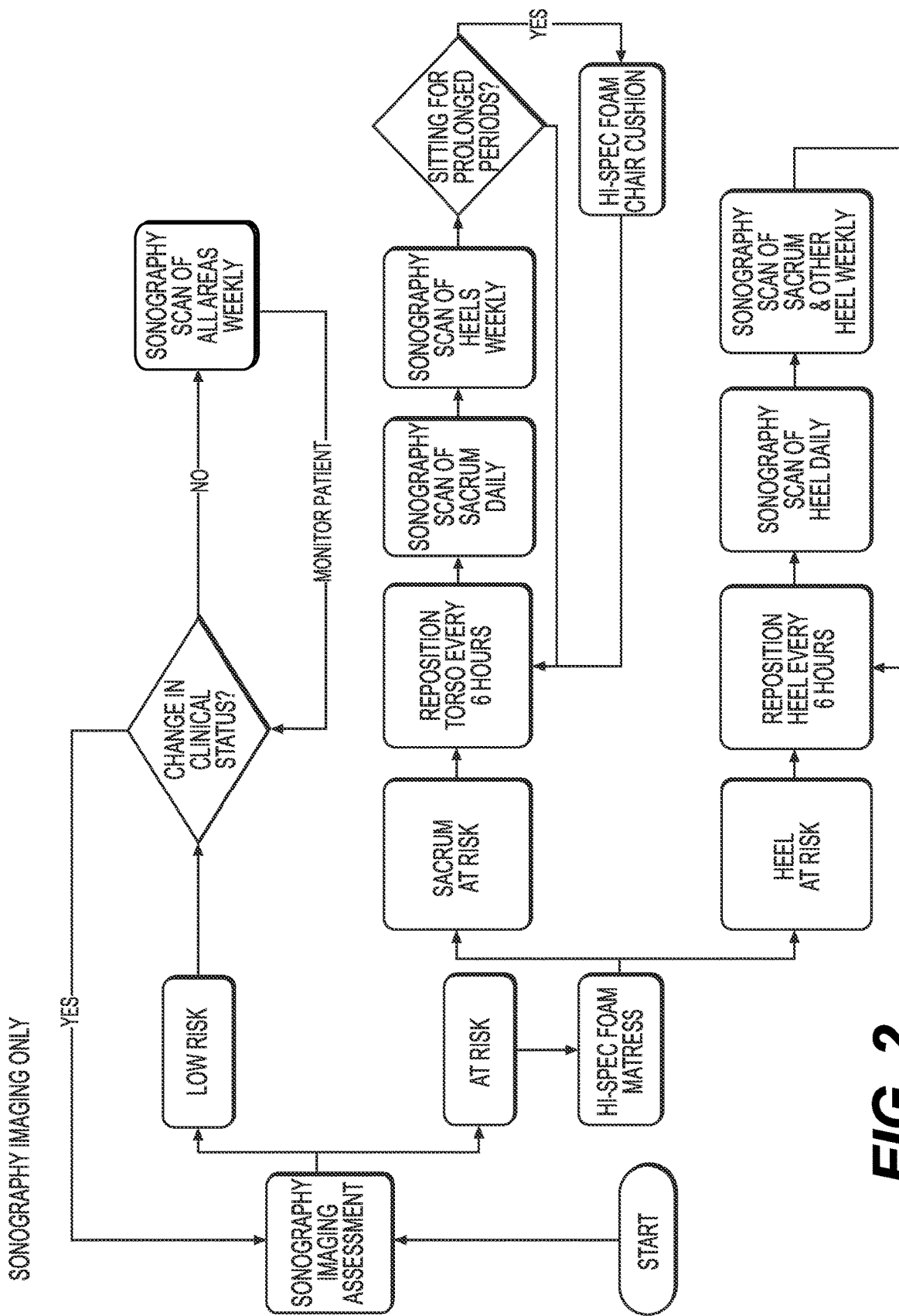
FIG. 2 is an example flowchart of how an apparatus for assessing sonographic characteristics in tissue below a patient's skin may be used in a stand-alone process to prevent pressure ulcers, in accordance with the present disclosure.

FIG. 2 is an example flowchart of how an apparatus of for assessing sonography images of tissue below a patient's skin may be used in a stand-alone process to prevent pressure ulcers, in accordance with the present disclosure. Every incoming patient receives a complete sonography imaging assessment of all body locations that are selected for monitoring. These selected locations may include areas recommended in the Instructions. For Use (IFU) of the sonography imaging apparatus, such as the sacrum and the heels. Additional locations may be identified by the hospital and integrated into their in-house practice. Multiple sonography images are taken at and around each body location at positions that are spatially distinct from each other. Sonographic characteristics for each location from the set of measurements are determined at and around that location. The number of sonographic characteristics is then compared to one or more threshold values to categorize a patient.

In this example, the patient is assigned to one of two risk categories: low-risk and at-risk. A low-risk patients receives weekly sonography imaging of all body locations that are selected for monitoring. This is a small cost that provides benefit for even the healthiest patients, as a weekly sonography imaging scans are more likely to detect tissue damage before it becomes visible to VSA.

At-risk patients, who will include patients that would have been identified as high-risk in the current care pathways of FIGS. 1A and 1B, will receive specialized care based on the body location that exhibits a number of sonographic characteristics above a threshold. For example, if the sacrum has a number of sonographic characteristics above a threshold, the patient will be repositioned every 6 hours and receive further sonography imaging of the sacrum every day, while other body locations like the heel receive weekly sonography imaging.

Figure 3:
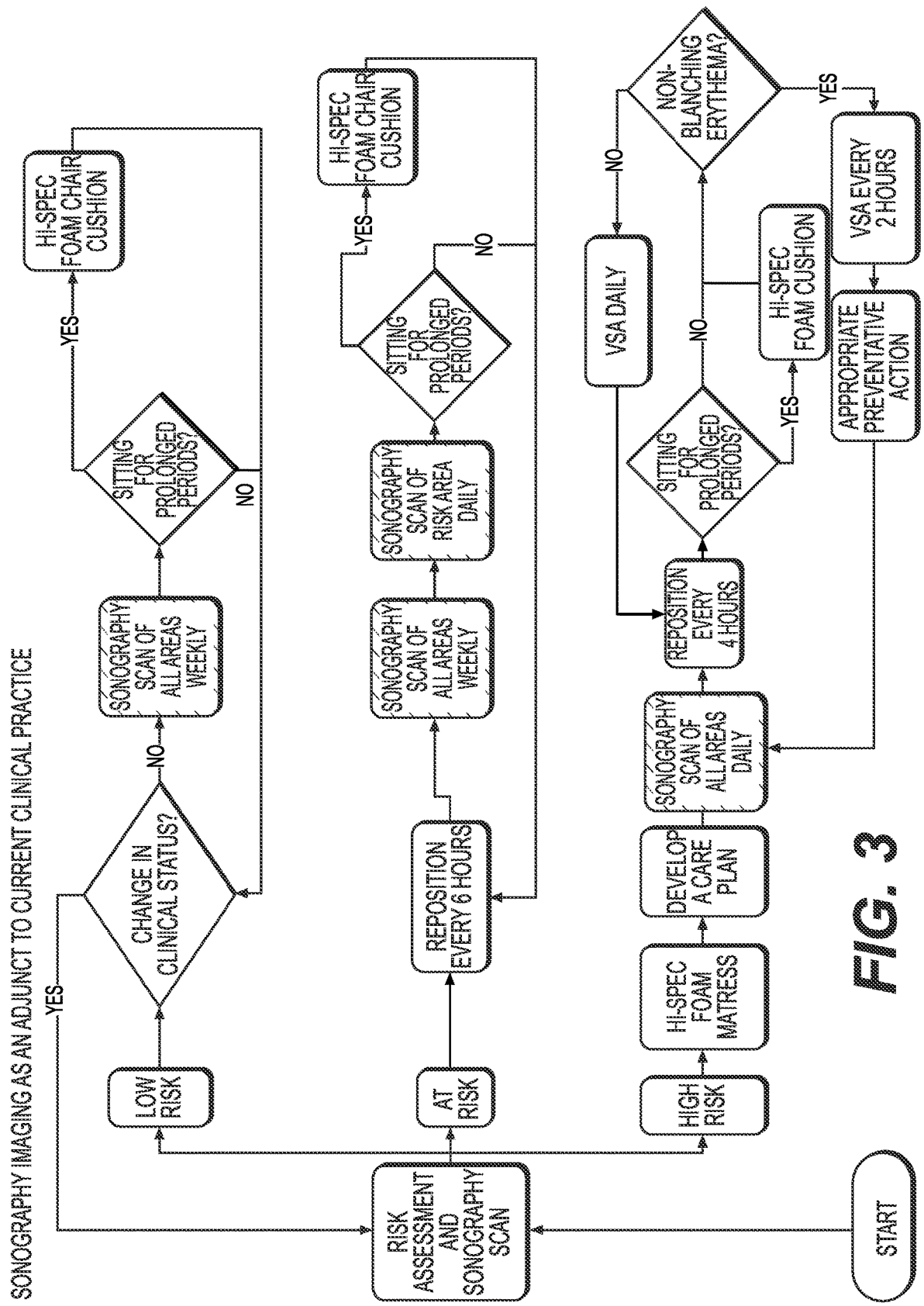
FIG. 3 is an example flowchart of how an apparatus for assessing sonographic characteristics in tissue below a patient's skin may be used as an adjunct to further improve the augmented treatment decision pathway of FIG. 1B, in accordance with the present disclosure.

FIG. 3 is a flowchart of how an apparatus of for sonography imaging tissue below a patient's skin may be used as an adjunct to further improve the augmented treatment decision pathway of FIG. 1B, in accordance with the present disclosure. An incoming patient receives both a risk assessment and a sonography imaging scan of all body locations identified by the hospital for monitoring, and the assignment of a patient to a risk category is based partially on the risk assessment and partially on the sonography imaging scan results. An initial number of sonographic characteristics that is greater than a threshold is an indication that there is possible damage at that body location.

A decision whether to implement an intervention, for example turning the patient at a first interval, is currently based on the VSA and risk assessment despite the uncertainty of whether there is early stage damage below the skin. However, when sonography imaging is used as an adjunct to the augmented treatment decision pathway as shown in FIG. 3, the decision to implement an intervention at a particular body location, or a general intervention such as a high-spec mattress, is based on the number of sonographic characteristics found for that site in the sonography imaging scan. If the number of sonographic characteristics is less than a predetermined threshold, no intervention is required. If the number of sonographic characteristics is greater than the predetermined threshold, then an intervention is selected and implemented based partially on the body location and partially on the number of sonographic characteristics for that body location. The predetermined threshold for whether or not to select and implement an intervention may be higher or lower than the threshold for determination that there is possible damage at the body location.

A comparison of the costs of provided the care pathways of FIGS. 1A, 1B, 2, and 3 reveals one of the benefits of utilizing a sonography imaging apparatus to monitor patients. Note that the costs cited herein are for patients who do not have or develop pressure ulcers, in which case the estimated treatment cost jumps to $2000 for a Stage 1 ulcer.

The baseline for this comparison is the augmented current practice of FIG. 1B, which represents a current "best practice" for hospitals striving to reduce the incidence rate of pressure ulcers. Providing the care of the low-risk care pathway is expected to cost an average of $26 per patient for the average hospital stay of 5.6 days, while the care for an at-risk patient is estimated to cost an average of $121, and that for a high-risk patient is expected to cost $165. All of the current care pathways rely on a VSA to detect a pressure ulcer and are otherwise implementing interventions based on "typical" patient progression rather than the particular patient's condition.

Integrating a sonography imaging apparatus into the current "best practice" workflow, as shown in FIG. 3, does not lower the cost of any of the care pathways as no work element is being eliminated. However, the benefit lies in the ability to detect tissue damage at an earlier stage at a minimal incremental cost. The incremental cost of adding a sonography imaging scan to the low-risk care pathway is $2, raising the cost from approximately $26 to $28. The expected cost of caring for an at-risk patient who does not have any elevated number of sonographic characteristics, i.e. does not have subepidermal tissue damage, is also increased by only $2. If an at-risk patient is found to have an elevated number of sonographic characteristics, however, the patient is escalated to the high-risk category, where the expected cost of care increases from $165 to $169. This represents a small additional cost for the benefit of earlier detection of tissue damage in low-risk and at-risk patients.

FIG. 2 represents an example workflow that forgoes the routine VSA and relies solely on a sonography imaging apparatus to monitor patients. The expected cost of preventative care for a low-risk patient is $4 using sonography imaging only, compared to the $28 cost using the integrated low-risk care pathway of FIG. 3. For an at-risk patient using sonography imaging only as shown in FIG. 2, the expected cost is $97, compared to the $123-$169 costs for the at-risk and high-risk patients of the integrated care pathway of FIG. 3.

Example 4: Risk Levels Based on Number of Sonographic Characteristics

Subjects identified as being at risk for pressure ulcers are treated in accordance with the following scheme:

One or more sonography images of the patient at one or more target body locations are obtained. For each body location scanned, the number of sonographic characteristics is determined. The number of sonographic characteristics at different body locations of a number of patients with and without pressure injuries had previously been taken, and used to construct a histogram of the number of sonographic characteristics. As shown in Table 3, a patient with a number of sonographic characteristics less than 3 is assigned to a risk level of zero. A patient with a number of sonographic characteristics that falls greater or equal to three and less than ten is assigned to a risk level of one. A patient with a number of sonographic characteristics greater or equal to ten is assigned to a risk level of two. Appropriate interventions corresponding to the assigned risk levels are performed. Subsequent sonography imaging is also performed at a frequency determined by the assigned intervention level. The assigned intervention level of the patient may be changed (increased or decreased) or kept the same depending on the number of sonographic characteristics of the subsequent measurements.

TABLE 3

EXAMPLE INTERVENTION SCHEME FOR TREATING A PATIENT AT RISK FOR PRESSURE ULCER

| Risk Level | Intervention | Frequency of Subsequent Sonography Imaging | Corresponding Sonographic characteristics Ranges |
|---|---|---|---|
| 0 | provide good nutrition, standard mattress, and/or turn every 24 hours | every 24 hours | SC < 3 |
| 1 | provide a heel boot; apply dressing to back or sides of anatomic sites at risk; change of support surfaces; turn patient at a shorter interval | every 4 hours | 3 ≤ SC < 10 |
| 2 | provide a low-friction padded mattress surface; keep patient's body dry; turn every 1-2 hours | every 1 hour | SC ≥ 10 |

From the foregoing, it will be appreciated that the present invention can be embodied in various ways, which include but are not limited to the following:

Embodiment 1. An apparatus for producing sonographic images of tissue below a patient's intact skin, comprising: (a) an emitter configured to emit sound waves at an intermediate frequency of about 10 MHz when activated; (b) a receiver configured to received returned sound waves vibrations, and convert the vibrations into electrical pulses; and (c) a processor coupled to the receiver, and configured to: (i) receive electrical pulses from the receiver; (ii) determine the length of time for the sound waves to return; (iii) determine the intensity of the returned sound waves; and (iv) generate a sonography image.

Embodiment 2. The apparatus of embodiment 1, further comprising a display configured to receive the sonography image and provide the sonography image on the display.

Embodiment 3. A method of assessing sonographic characteristics in a tissue below a patient's intact skin, the method comprising the steps of: (a) emitting sound waves into the patient's skin at a first location; (b) receiving a portion of the returned sound waves that have been echoed from the tissue; (c) determining the length of time for the sound waves to return; (d) determining the intensity of the returned sound waves; (e) generating a sonography image; (f) obtaining the sonography image; and (g) obtaining the number and type of one or more sonographic characteristics.

Embodiment 4. The method of embodiment 3, wherein the one or more sonographic characteristics is selected from the group consisting of unclear layered structure, hypoechoic lesion, discontinuous fascia, and heterogeneous hypoechoic area.

Embodiment 5. A method for reducing the incidence of wound development in patients admitted to a care facility, the method comprising the steps of: (a) evaluating a patient for a risk of tissue damage upon admission to the care facility, wherein evaluating comprises: (i) obtaining a sonography image of the patient at one or more body locations at risk of wound development; and (ii) determining a number of sonographic characteristics of tissue damage present in the sonography image; (b) administering an intervention of level-0 if the number of sonographic characteristics present is below or equal to a first threshold; and (c) administering an intervention of level-N if the number of sonographic characteristics present exceeds the first threshold, wherein N is an integer ≥1.

Embodiment 6. The method of embodiment 5, wherein the sonographic characteristic is selected from the group consisting of unclear layered structure, hypoechoic lesion, discontinuous fascia, and heterogeneous hypoechoic area.

Embodiment 7. The method of embodiment 5, wherein the sonographic characteristic is unclear layered structure.

Embodiment 8. The method of embodiment 5, wherein the sonographic characteristic is hypoechoic lesion.

Embodiment 9. The method of embodiment 5, wherein the sonographic characteristic is discontinuous fascia.

Embodiment 10. The method of embodiment 5, wherein the sonographic characteristic is heterogeneous hypoechoic area.

Embodiment 11. The method of any one of embodiments 5-10, wherein the wound is selected from the group consisting of a pressure ulcer, a diabetic foot ulcer, deep tissue injury, a vascular ulcer, and a burn wound.

Embodiment 12. The method of any one of embodiments 5-11, wherein the one or more body locations at risk of wound development is selected from the group consisting of a sternum, a sacrum, a heel, a scapula (os latum scapularum), an elbow, an ear, and other fleshy tissues over a bony prominence of a patient.

Embodiment 13. The method of any one of embodiments 5-12, wherein the one or more body locations at risk of wound development comprises an anatomical site in long-term contact with a medical device.

Embodiment 14. The method of any one of embodiments 5-13, wherein the one or more body locations at risk of wound development is selected from the group consisting of a cheek, a nose, a chest, a stomach, and a lower abdomen area.

Embodiment 15. The method of any one of embodiments 5-14, wherein the intervention of level-N is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

Embodiment 16. A method of stratifying a plurality of patients in a care facility based on care levels, the method comprising the steps of: (a) obtaining a sonography image of a patient in the plurality of patients at one or more body locations selected for monitoring; (b) determining whether a sonographic characteristic of tissue damage is present in the sonography image; (c) determining a care level of N care levels that corresponds to the number and type of sonographic characteristic present; (d) assigning the care level to the patient based on step (c); and (e) arranging the patient of the plurality of patients into groups based on the patient's assigned care levels.

Embodiment 17. The method of embodiment 16, wherein the sonographic characteristic is selected from the group consisting of unclear layered structure, hypoechoic lesion, discontinuous fascia, and heterogeneous hypoechoic area.

Embodiment 18. The method of embodiment 16 or 17, wherein the sonographic characteristic is a discontinuous fascia.

Embodiment 19. The method of any one of embodiments 16-18, wherein the one or more body locations is selected from the group consisting of a sternum, a sacrum, a heel, a scapula (os latum scapularum), an elbow, an ear, and other fleshy tissues over a bony prominence of a patient.

Embodiment 20. The method of any one of embodiments 16-19, wherein the one or more body locations comprises an anatomical site in long-term contact with a medical device.

Embodiment 21. The method of any one of embodiments 16-20, wherein the one or more body locations is selected from the group consisting of a cheek, a nose, a chest, a stomach, and a lower abdomen area.

Embodiment 22. The method of any one of embodiments 16-21, wherein assigning a care level to the patient is based on the presence or absence of discontinuous fascia.

Embodiment 23. The method of any one of embodiments 16-22, wherein assigning a care level to the patient is based on a change in the presence of unclear layered structure over a period of two weeks.

Embodiment 24. A method for identifying and providing an appropriate level of care to a patient in a care facility, the method comprising the steps of: (a) obtaining a plurality of sonography images of the patient at one or more body locations; (b) determining whether a sonographic characteristic of tissue damage is present in the plurality of sonography images; (c) providing one or more anatomy-specific interventions based on the presence or absence of sonographic characteristics in step (b); (d) increasing the level of anatomy-specific interventions based on an increase in the number of sonographic characteristics; and (e) decreasing the level of anatomy-specific interventions based on a decrease in the number of sonographic characteristics.

Embodiment 25. The method of embodiment 24, wherein the sonographic characteristic is selected from the group consisting of unclear layered structure, hypoechoic lesion, discontinuous fascia, and heterogeneous hypoechoic area.

Embodiment 26. The method of embodiment 24 or 25, wherein the sonographic characteristic is a discontinuous fascia.

Embodiment 27. The method of embodiment 24 or 25, wherein the sonographic characteristic is unclear layered structure.

Embodiment 28. The method of any one of embodiments 24-27 wherein the one or more body locations is selected from the group consisting of a sternum, a sacrum, a heel, a scapula (os latum scapularum), an elbow, an ear, and other fleshy tissues over a bony prominence of a patient.

Embodiment 29. The method of any one of embodiments 24-28, wherein the one or more body locations comprises an anatomical site in long-term contact with a medical device.

Embodiment 30. The method of any one of embodiments 24-29, wherein the one or more body locations is selected from the group consisting of a cheek, a nose, a chest, a stomach, and a lower abdomen area.

Embodiment 31. The method of any one of embodiments 24-30, wherein the anatomy-specific intervention is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

Embodiment 32. The method of any one of embodiments 24-31, wherein the level of anatomy-specific interventions is increased if the number of sonographic characteristics exceeds a first threshold.

Embodiment 33. The method of any one of embodiments 24-32, wherein the level of anatomy-specific interventions is decreased if the number of sonographic characteristics falls below a second threshold.

Embodiment 34. A method for assigning a patient in a care facility to a risk category selected from a plurality of risk categories, the method comprising the steps of: (a) obtaining a plurality of initial sonography images of the patient at one or more body locations selected for monitoring; (b) determining whether a sonographic characteristic is present in the plurality of sonography images; and (c) assigning the patient to a risk category selected from the plurality of risk categories wherein the assigning is based partially on the presence or absence of sonographic characteristics in step (b).

Embodiment 35. The method of embodiment 34, wherein the sonographic characteristic is selected from the group consisting of unclear layered structure, hypoechoic lesion, discontinuous fascia, and heterogeneous hypoechoic area.

Embodiment 36. The method of embodiment 34 or 35, wherein the sonographic characteristic is a discontinuous fascia.

Embodiment 37. The method of embodiment 34 or 35, wherein the sonographic characteristic is unclear layered structure.

Embodiment 38. The method of any one of embodiments 34-37, wherein the one or more body locations selected for monitoring is selected from the group consisting of a sternum, a sacrum, a heel, a scapula (os latum scapularum), an elbow, an ear, and other fleshy tissues over a bony prominence of a patient.

Embodiment 39. The method of any one of embodiments 34-38, wherein the one or more body locations selected for monitoring comprises an anatomical site in long-term contact with a medical device.

Embodiment 40. The method of any one of embodiments 34-39, wherein the one or more body locations selected for monitoring is selected from the group consisting of a cheek, a nose, a chest, a stomach, and a lower abdomen area.

Embodiment 41. A method for managing care of a patient in a care facility, the method comprising the steps of: (a) obtaining a plurality of first sonography images of the patient at one or more body locations selected for monitoring upon admission to a care facility; (b) determining whether a sonographic characteristic is present in the plurality of first sonography images; (c) setting an intervention level to N=1 if the number of sonographic characteristics present is above a first threshold; (d) implementing a level-N intervention for each of the one or more body location having a number of sonographic characteristics present above the first threshold; (e) obtaining a plurality of subsequent sonography images at each of the one or more body locations at a level-N frequency; and (f) determining if new sonographic characteristics are present in the plurality of subsequent sonography images.

Embodiment 42. The method of embodiment 41, wherein the sonographic characteristic is selected from the group consisting of unclear layered structure, hypoechoic lesion, discontinuous fascia, and heterogeneous hypoechoic area.

Embodiment 43. The method of embodiment 41 or 42, wherein the sonographic characteristic is a discontinuous fascia.

Embodiment 44. The method of embodiment 41 or 42, wherein the sonographic characteristic is unclear layered structure.

Embodiment 45. The method of any one of embodiments 41-44 wherein the body location selected for monitoring is selected from the group consisting of a sternum, a sacrum, a heel, a scapula (os latum scapularum), an elbow, an ear, and other fleshy tissues over a bony prominence of a patient.

Embodiment 46. The method of any one of embodiments 41-45, wherein the body location selected for monitoring comprises an anatomical site in long-term contact with a medical device.

Embodiment 47. The method of any one of embodiments 41-46, wherein the body location selected for monitoring is selected from the group consisting of a cheek, a nose, a chest, a stomach, and a lower abdomen area.

Embodiment 48. The method of any one of embodiment 41-47, wherein the level-N intervention is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

Embodiment 49. A method of identifying and treating a patient at risk of tissue damage, the method comprising the steps of: (a) evaluating a patient for a risk of tissue damage upon admission to a care facility, wherein the evaluating step comprises: (i) obtaining a first plurality of sonography images in the patient; and (ii) determining a first number of sonographic characteristics present in the first plurality of sonography images; (b) administering a first intervention of level-0 if the first number of sonographic characteristics present is below or equal to a first threshold; and (c) administering a first intervention of level-N if the first number of sonographic characteristics present is above the first threshold, where N is an integer and N has a value of 1 or greater.

Embodiment 50. The method of embodiment 49, further comprising the steps of: (a) obtaining a second plurality of sonography images in the patient at a first pre-determined frequency corresponding to the administered intervention level; (b) determining a second number of sonographic characteristics present in the second plurality of sonography images; (c) determining whether the second number of sonographic characteristics exceeds a second threshold; (d) continuing to administer the first intervention if the second number of sonographic characteristics present does not exceed the second threshold; (e) continuing to take a plurality of sonography images at the first pre-determined frequency if the second number of sonographic characteristics present does not exceed the second threshold; (f) administering a second intervention of level-M if the second number of sonographic characteristics present exceeds the second threshold, where M is an integer and M is greater than N; and (g) obtaining a third plurality of sonography images at a pre-determined frequency corresponding to level-M if the second number of sonographic characteristics present exceeds the second threshold.

Embodiment 51. The method of embodiment 49 or 50, further comprising the steps of: (a) determining whether the second number of sonographic characteristics present is below or equal to a third threshold; (b) continuing to administer the first intervention if the second number of sonographic characteristics present is not less than a third threshold; (c) continuing to take a plurality of sonography images at the first pre-determined frequency if the second number of sonographic characteristics present is not less than the third threshold;

(d) administering a third intervention of level-L if the second number of sonographic characteristics present is less than the third threshold and if the first intervention is not of level-0, where L is an integer and L is less than N; and (e) obtaining a plurality of sonography images at a pre-determined frequency corresponding to level-L if the second number of sonographic characteristics present is less than a third threshold.

Embodiment 52. The method of any one of embodiment 49-51, wherein the first intervention of level-N is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

Embodiment 53. The method of any one of embodiment 50-52, wherein the second intervention of level-M is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

Embodiment 54. The method of any one of embodiment 51-53, wherein the third intervention of level-L is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

Embodiment 55. The method of any one of embodiments 49-54, wherein the sonographic characteristics are selected from the group consisting of unclear layered structure, hypoechoic lesion, discontinuous fascia, and heterogeneous hypoechoic area.

Embodiment 56. The method of any one of embodiments 49-55, wherein the sonographic characteristic is a discontinuous fascia.

Embodiment 57. The method of any one of embodiments 49-55, wherein the sonographic characteristic is unclear layered structure.

Embodiment 58. The method of any one of embodiments 49-57 wherein the first plurality of sonography images is obtained at or around one or more body locations selected from the group consisting of a sternum, a sacrum, a heel, a scapula (os latum scapularum), an elbow, an ear, and other fleshy tissues over a bony prominence of a patient.

Embodiment 59. The method of any one of embodiments 49-58, wherein the first plurality of sonography images is obtained at or around an anatomical site in long-term contact with a medical device.

Embodiment 60. The method of any one of embodiments 49-59, wherein the first plurality of sonography images is obtained at or around one or more body locations selected from the group consisting of a cheek, a nose, a chest, a stomach, and a lower abdomen area.

Embodiment 61. A method of slowing the progression of skin and tissue damage in a patient in need thereof, the method comprising the steps of: (a) identifying a current intervention of level-K received by the patient; (b) obtaining a plurality of sonography images in the patient; (c) identifying a sonographic characteristic in the plurality of sonography images; (d) determining a first number of sonographic characteristics present in the plurality of sonography images; (e) continuing to administer the current intervention of level-K if the first number of sonographic characteristics is below or equal to a first threshold; (f) continuing to take a plurality of sonography images at a pre-determined frequency corresponding to level-K if the first number of sonographic characteristics is below or equal to the first threshold; (g) administering a new intervention of level-N if the number of sonographic characteristics exceeds the first threshold, where N has a value greater than K; and (h) taking a plurality of sonography images at a pre-determined frequency corresponding to level-N if the number of sonographic characteristics exceeds the first threshold.

Embodiment 62. The method of embodiment 61, further comprising the steps of: (a) determining whether the first number of sonographic characteristics present is less than a second threshold; (b) administering an intervention of level-L if the first number of sonographic characteristics is less than a second threshold, where L has a non-negative value lesser than K; and (c) obtaining a plurality of sonography images at a pre-determined frequency corresponding to level-L if the first number of sonographic characteristics is less than the second threshold.

Embodiment 63. The method of embodiment 61 or 62, wherein the sonographic characteristic is selected from the group consisting of unclear layered structure, hypoechoic lesion, discontinuous fascia, and heterogeneous hypoechoic area.

Embodiment 64. The method of embodiment 61 or 62, wherein the sonographic characteristic is a discontinuous fascia.

Embodiment 65. The method of embodiment 61 or 62, wherein the sonographic characteristic is unclear layered structure.

Embodiment 66. The method of embodiment 61 or 62, wherein the sonographic characteristic is hypoechoic lesion.

Embodiment 67. The method of embodiment 61 or 62, wherein the sonographic characteristic is heterogeneous hypoechoic area.

Embodiment 68. The method of any one of embodiments 61-67 wherein the plurality of sonography images is obtained at or around one or more body locations selected from the group consisting of a sternum, a sacrum, a heel, a scapula (os latum scapularum), an elbow, an ear, and other fleshy tissues over a bony prominence of a patient.

Embodiment 69. The method of any one of embodiments 61-68, wherein the plurality of sonography images is obtained at or around an anatomical site in long-term contact with a medical device.

Embodiment 70. The method of any one of embodiments 61-69, wherein the plurality of sonography images is obtained at or around one or more body locations selected from the group consisting of a cheek, a nose, a chest, a stomach, and a lower abdomen area.

Embodiment 71. A method of identifying and treating a patient in need of an intervention, the method comprising the steps of: (a) obtaining a plurality of sonography images at an anatomic site of the patient; (b) identifying a sonographic characteristic in the plurality of sonography images; (c) determining a number of sonographic characteristics from the plurality of sonography images; (d) determining whether the number of sonographic characteristics exceeds a threshold corresponding to level-N, where N is greater than or equal to 2; (e) administering the intervention to the anatomic site if the number of sonographic characteristics exceeds the threshold; and (f) taking a plurality of sonography images every two hours if the number of sonographic characteristic exceeds the threshold.

Embodiment 72. The method of embodiment 71, wherein the sonographic characteristic is selected from the group consisting of unclear layered structure, hypoechoic lesion, discontinuous fascia, and heterogeneous hypoechoic area.

Embodiment 73. The method of embodiment 71 or 72, wherein the sonographic characteristic is a hypoechoic lesion.

Embodiment 74. The method of any one of embodiments 71-73, wherein the anatomical site is selected from the group consisting of a sternum, a sacrum, a heel, a scapula (os latum scapularum), an elbow, an ear, and other fleshy tissues over a bony prominence of a patient.

Embodiment 75. The method of any one of embodiments 71-74, wherein the intervention is selected from the group consisting of a heel boot, a barrier cream, neuromuscular stimulation, a topical cream, therapeutic ultrasound, shockwave therapy, a 30-degree wedge, a composite dressing, a hybrid mattress, a dynamic mattress, a support surface, a silicone pad, a low-friction sheet cover, and a low-friction padded mattress surface.

Embodiment 76. A method for identifying damaged tissue, the method comprising the steps of: (a) obtaining a first sonography image from a first location on a patient's skin; (b) obtaining a second sonography image from a second location that is bisymmetric relative to the first location; (c) identifying sonographic characteristics in each of the first and second sonography images; (d) determining the number of sonographic characteristics from each of the first and second sonography image; (e) determining a difference in the number of sonographic characteristics between a first sonography image and a second sonography image, and (f) determining that there is tissue damage at the first or second location if the difference in the number of sonographic characteristics between the first sonography image and the second sonography image exceeds a threshold value.

Embodiment 77. The method of embodiment 76, wherein the sonographic characteristic is selected from the group consisting of unclear layered structure, hypoechoic lesion, discontinuous fascia, and heterogeneous hypoechoic area.

Embodiment 78. The method of embodiment 76 or 77, wherein the sonographic characteristic is a discontinuous fascia.

Embodiment 79. The method of any one of embodiments 76-78, wherein the location is selected from the group consisting of a sternum, a sacrum, a heel, a scapula (os latum scapularum), an elbow, an ear, and other fleshy tissues over a bony prominence of a patient.

Embodiment 80. A method of detecting tissue damage before it is visible on a patient's skin, the method comprising the steps of: (a) obtaining a plurality of sonography images at a single location at incremental times; (b) identifying sonographic characteristics in each of the plurality of sonography images; (c) determining the number of sonographic characteristics from each of the plurality of sonography images; (d) calculating a slope between the latest number of sonographic characteristics and the immediately prior number of sonographic characteristics; (e) comparing the slope to a threshold value; and (f) determining that there is tissue damage if the slope exceeds the threshold value.

Embodiment 81. The method of embodiment 80, wherein the sonographic characteristic is selected from the group consisting of unclear layered structure, hypoechoic lesion, discontinuous fascia, and heterogeneous hypoechoic area.

Embodiment 82. The method of embodiment 80 or 81, wherein the sonographic characteristic is a discontinuous fascia.

Embodiment 83. The method of any one of embodiments 80-82, wherein the location is selected from the group consisting of a sternum, a sacrum, a heel, a scapula (os latum scapularum), an elbow, an ear, and other fleshy tissues over a bony prominence of a patient.

Embodiment 84. A method of detecting tissue damage before it is visible on a patient's skin, the method comprising the steps of: (a) obtaining a plurality of sonography images at a single location at incremental times; (b) identifying sonographic characteristics in each of the plurality of sonography images; (c) determining the number of sonographic characteristics from each of the plurality of sonography images; (d) calculating a difference value of the maximum number of sonographic characteristics and the minimum number of sonographic characteristics for each incremental time; (e) calculating a derivative of the difference value with respect to time; (f) comparing the derivative to a threshold value; and (g) determining that there is tissue damage if the derivative exceeds the threshold value.

Embodiment 85. The method of embodiment 84, wherein the sonographic characteristic is selected from the group consisting of unclear layered structure, hypoechoic lesion, discontinuous fascia, and heterogeneous hypoechoic area.

Embodiment 86. The method of embodiment 84 or 85, wherein the sonographic characteristic is a discontinuous fascia.

Embodiment 87. The method of any one of embodiments 84-86, wherein the location is selected from the group consisting of a sternum, a sacrum, a heel, a scapula (os latum scapularum), an elbow, an ear, and other fleshy tissues over a bony prominence of a patient.

Embodiment 88. A method of detecting tissue damage before it is visible on a patient's skin, the method comprising the steps of: (a) obtaining a plurality of sonography images at a single location at incremental times; (b) identifying sonographic characteristics in each of the plurality of sonography images; (c) determining the number of sonographic characteristics from each of the plurality of sonography images; (d) calculating a difference value of the maximum number of sonographic characteristics and the minimum number of sonographic characteristics for each incremental time; (e) fitting a curve to a predetermined number of the most-recent difference values; (f) calculating a curvature of the fitted curve; (g) comparing the curvature to a threshold value; and (h) determining that there is tissue damage if the curvature exceeds the threshold value.

Embodiment 89. The method of embodiment 88, wherein the sonographic characteristic is selected from the group consisting of unclear layered structure, hypoechoic lesion, discontinuous fascia, and heterogeneous hypoechoic area.

Embodiment 90. The method of embodiment 88 or 89, wherein the sonographic characteristic is a discontinuous fascia.

Embodiment 91. The method of any one of embodiments 88-90, wherein the location is selected from the group consisting of a sternum, a sacrum, a heel, a scapula (os latum scapularum), an elbow, an ear, and other fleshy tissues over a bony prominence of a patient.

While the invention has been described with reference to particular aspects, it will be understood by those skilled in the art that various changes may be made and equivalents may be substituted for elements thereof without departing from the scope of the invention. In addition, many modifications may be made to a particular situation or material to the teachings of the invention without departing from the scope of the invention. Therefore, it is intended that the invention not be limited to the particular aspects disclosed but that the invention will include all aspects falling within the scope and spirit of the appended claims.

I claim:

1. A method for reducing the incidence of wound development in patients admitted to a care facility, the method comprising the steps of:
   a. evaluating a patient for a risk of tissue damage upon admission to the care facility, wherein evaluating comprises:
      i. obtaining a sonography image of the patient at one or more body locations at risk of wound development; and
      ii. determining a number of sonographic characteristics of tissue damage present in the sonography image;
   b. if the number of sonographic characteristics present is below or equal to a first threshold, performing (1) administering a level-0 intervention, and (2) obtaining a subsequent sonography image of the one or more body locations after a time interval associated with level-0 transpires; and
   c. if the number of sonographic characteristics present exceeds the first threshold, performing (1) administering a level-N intervention, and (2) obtaining a subsequent sonography image of the one or more body locations after a time interval associated with level-N transpires, and wherein N is an integer $\geq 1$.

2. The method of claim 1, wherein the sonographic characteristic is selected from the group consisting of unclear layered structure, hypoechoic lesion, discontinuous fascia, and heterogeneous hypoechoic area.

3. A method for identifying and providing an appropriate level of care to a patient in a care facility, the method comprising the steps of:
   a. obtaining a plurality of sonography images of the patient at one or more body locations, wherein the one or more body locations is selected from the group consisting of a sternum, a sacrum, a heel, a scapula, an elbow, an ear, and other fleshy tissue over a bony prominence of the patient;
   b. determining whether a sonographic characteristic of tissue damage is present in the plurality of sonography images;
   c. providing one or more anatomy-specific interventions to the one or more body locations based on the presence or absence of sonographic characteristics in step (b);
   d. increasing the level of anatomy-specific interventions to the one or more body locations based on an increase in the number of sonographic characteristics; and
   e. decreasing the level of anatomy-specific interventions to the one or more body locations based on a decrease in the number of sonographic characteristics.

4. The method of claim 3, wherein the sonographic characteristic is selected from the group consisting of unclear layered structure, hypoechoic lesion, discontinuous fascia, and heterogeneous hypoechoic area.

5. The method of claim 3, wherein the level of anatomy-specific interventions is increased if the number of sonographic characteristics exceeds a first threshold.

6. The method of claim 3, wherein the level of anatomy-specific interventions is decreased if the number of sonographic characteristics falls below a second threshold.

7. A method for managing care of a patient in a care facility, the method comprising the steps of:

a. obtaining a plurality of first sonography images of the patient at one or more body locations selected for monitoring upon admission to a care facility;
b. determining whether a sonographic characteristic is present in the plurality of first sonography images;
c. setting an intervention level to N=1 if the number of sonographic characteristics present is above a first threshold;
d. implementing a level-N intervention for each of the one or more body location having a number of sonographic characteristics present above the first threshold;
e. obtaining a plurality of subsequent sonography images at each of the one or more body locations at a frequency corresponding to level-N; and
f. determining if new sonographic characteristics are present in the plurality of subsequent sonography images.

8. The method of claim 7, wherein the sonographic characteristic is selected from the group consisting of unclear layered structure, hypoechoic lesion, discontinuous fascia, and heterogeneous hypoechoic area.

9. A method of identifying and treating a patient at risk of tissue damage, the method comprising the steps of:
a. evaluating a patient for a risk of tissue damage upon admission to a care facility, wherein the evaluating step comprises:
  i. obtaining a first plurality of sonography images in the patient; and
  ii. determining a first number of sonographic characteristics present in the first plurality of sonography images;
b. if the first number of sonographic characteristics present is below or equal to a first threshold, performing (1) administering a first intervention of level 0, and (2) obtaining a second plurality of sonography images in the patient at a first pre-determined frequency corresponding to the administered intervention level; and
c. if the first number of sonographic characteristics present is above the first threshold, performing (1) administering a first intervention of level-N, and (2) obtaining a second plurality of sonography images in the patient at a first pre-determined frequency corresponding to the administered intervention level, where N is an integer and N has a value of 1 or greater.

10. The method of claim 9, further comprising the steps of:
a. determining a second number of sonographic characteristics present in the second plurality of sonography images;
b. determining whether the second number of sonographic characteristics exceeds a second threshold;
c. continuing to administer the first intervention if the second number of sonographic characteristics present does not exceed the second threshold;
d. continuing to take a plurality of sonography images at the first pre-determined frequency if the second number of sonographic characteristics present does not exceed the second threshold;
e. administering a second intervention of level-M if the second number of sonographic characteristics present exceeds the second threshold, where M is an integer and M is greater than N; and
f. obtaining a third plurality of sonography images at a pre-determined frequency corresponding to level-M if the second number of sonographic characteristics present exceeds the second threshold.

11. The method of claim 10, further comprising the steps of:
a. determining whether the second number of sonographic characteristics present is below or equal to a third threshold;
b. continuing to administer the first intervention if the second number of sonographic characteristics present is not less than a third threshold;
c. continuing to take a plurality of sonography images at the first pre-determined frequency if the second number of sonographic characteristics present is not less than the third threshold;
d. administering a third intervention of level-L if the second number of sonographic characteristics present is less than the third threshold and if the first intervention is not of level-0, where L is an integer and L is less than N; and
e. obtaining a plurality of sonography images at a pre-determined frequency corresponding to level-L if the second number of sonographic characteristics present is less than a third threshold.

12. The method of claim 9, wherein the sonographic characteristics are selected from the group consisting of unclear layered structure, hypoechoic lesion, discontinuous fascia, and heterogeneous hypoechoic area.

13. A method of slowing the progression of skin and tissue damage in a patient in need thereof, the method comprising the steps of:
a. identifying a current intervention of level-K received by the patient;
b. obtaining a plurality of sonography images in the patient;
c. identifying a sonographic characteristic in the plurality of sonography images;
d. determining a first number of sonographic characteristics present in the plurality of sonography images;
e. continuing to administer the current intervention of level-K if the first number of sonographic characteristics is below or equal to a first threshold;
f. continuing to take a plurality of sonography images at a pre-determined frequency corresponding to level-K if the first number of sonographic characteristics is below or equal to the first threshold;
g. administering a new intervention of level-N if the number of sonographic characteristics exceeds the first threshold, where N has a value greater than K; and
h. taking a plurality of sonography images at a pre-determined frequency corresponding to level-N if the number of sonographic characteristics exceeds the first threshold.

14. The method of claim 13, further comprising the steps of:
a. determining whether the first number of sonographic characteristics present is less than a second threshold;
b. administering an intervention of level-L if the first number of sonographic characteristics is less than a second threshold, where L has a non-negative value lesser than K; and
c. obtaining a plurality of sonography images at a pre-determined frequency corresponding to level-L if the first number of sonographic characteristics is less than the second threshold.

15. The method of claim 13, wherein the sonographic characteristic is selected from the group consisting of unclear layered structure, hypoechoic lesion, discontinuous fascia, and heterogeneous hypoechoic area.

16. A method of identifying and treating a patient in need of an intervention, the method comprising the steps of:
   a. obtaining a plurality of sonography images at an anatomic site of the patient, wherein the anatomic site is selected from the group consisting of a sternum, a sacrum, a heel, a scapula, an elbow, an ear, and other fleshy tissue over a bony prominence of the patient;
   b. identifying a sonographic characteristic in the plurality of sonography images;
   c. determining a number of sonographic characteristics from the plurality of sonography images;
   d. determining whether the number of sonographic characteristics exceeds a threshold corresponding to level-N, where N is greater than or equal to 2;
   e. administering an anatomy-specific intervention to the anatomic site if the number of sonographic characteristics exceeds the threshold; and
   f. taking a plurality of sonography images every two hours if the number of sonographic characteristic exceeds the threshold.

17. A method for identifying damaged tissue, the method comprising the steps of:
   a. obtaining a first sonography image from a first location on a patient's skin;
   b. obtaining a second sonography image from a second location that is bisymmetric relative to the first location;
   c. identifying sonographic characteristics in each of the first and second sonography images;
   d. determining the number of sonographic characteristics from each of the first and second sonography image;
   e. determining a difference in the number of sonographic characteristics between a first sonography image and a second sonography image, and
   f. determining that there is tissue damage at the first or second location if the difference in the number of sonographic characteristics between the first sonography image and the second sonography image exceeds a threshold value.

18. A method of detecting tissue damage before it is visible on a patient's skin, the method comprising the steps of:
   a. obtaining a plurality of sonography images at a single location at incremental times;
   b. identifying sonographic characteristics in each of the plurality of sonography images;
   c. determining the number of sonographic characteristics from each of the plurality of sonography images;
   d. calculating a slope between the latest number of sonographic characteristics and the immediately prior number of sonographic characteristics;
   e. comparing the slope to a threshold value; and
   f. determining that there is tissue damage if the slope exceeds the threshold value.

19. A method of detecting tissue damage before it is visible on a patient's skin, the method comprising the steps of:
   a. obtaining a plurality of sonography images at a single location at incremental times;
   b. identifying sonographic characteristics in each of the plurality of sonography images;
   c. determining the number of sonographic characteristics from each of the plurality of sonography images;
   d. calculating a difference value of the maximum number of sonographic characteristics and the minimum number of sonographic characteristics for each incremental time;
   e. calculating a derivative of the difference value with respect to time;
   f. comparing the derivative to a threshold value; and
   g. determining that there is tissue damage if the derivative exceeds the threshold value.

20. A method of detecting tissue damage before it is visible on a patient's skin, the method comprising the steps of:
   a. obtaining a plurality of sonography images at a single location at incremental times;
   b. identifying sonographic characteristics in each of the plurality of sonography images;
   c. determining the number of sonographic characteristics from each of the plurality of sonography images;
   d. calculating a difference value of the maximum number of sonographic characteristics and the minimum number of sonographic characteristics for each incremental time;
   e. fitting a curve to a predetermined number of the most-recent difference values;
   f. calculating a curvature of the fitted curve;
   g. comparing the curvature to a threshold value; and
   h. determining that there is tissue damage if the curvature exceeds the threshold value.

* * * * *

UNITED STATES PATENT AND TRADEMARK OFFICE
CERTIFICATE OF CORRECTION

| | | |
|---|---|---|
| PATENT NO. | : 12,133,763 B2 | Page 1 of 1 |
| APPLICATION NO. | : 17/776759 | |
| DATED | : November 5, 2024 | |
| INVENTOR(S) | : Martin F. Burns | |

It is certified that error appears in the above-identified patent and that said Letters Patent is hereby corrected as shown below:

In the Claims

In Claim 9, Line 22 (Column 59): "where Nis an integer" should read -- where N is an integer --

Signed and Sealed this
Thirty-first Day of December, 2024

Derrick Brent
*Acting Director of the United States Patent and Trademark Office*